(12) United States Patent
O'Brien et al.

(10) Patent No.: US 6,559,142 B2
(45) Date of Patent: May 6, 2003

(54) SULFONAMIDE MATRIX METALLOPROTEINASE INHIBITORS

(75) Inventors: Patrick Michael O'Brien, Stockbridge, MI (US); William Chester Patt, Chelsea, MI (US); Joseph Armand Picard, Canton, MI (US); Kevon Ray Shuler, Chelsea, MI (US); Drago Robert Sliskovic, Saline, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/071,662

(22) Filed: Feb. 8, 2002

(65) Prior Publication Data

US 2002/0169160 A1 Nov. 14, 2002

Related U.S. Application Data

(60) Provisional application No. 60/268,737, filed on Feb. 14, 2001.

(51) Int. Cl.[7] .................... C07D 279/12; C07D 417/12; C07D 417/14; A61K 31/54
(52) U.S. Cl. ................. 514/228.2; 514/211.01; 514/365; 540/544; 544/60; 548/200; 548/201
(58) Field of Search ............. 544/60; 514/228.2, 514/365, 211.01; 548/200, 201; 540/544

(56) References Cited

U.S. PATENT DOCUMENTS

| 5,948,780 A | 9/1999 | Peterson, Jr. et al. ........ 514/255 |
| 6,008,243 A | 12/1999 | Bender et al. ............... 514/422 |

FOREIGN PATENT DOCUMENTS

| WO | WO 97/18194 | 5/1997 |
| WO | WO 98/09934 | 3/1998 |
| WO | WO 98/34918 | 8/1998 |
| WO | WO 01/63244 A1 | 8/2001 |

OTHER PUBLICATIONS

Creemers et al., PubMed Abstract (Circ. Res. 89(3):201–10), Aug. 2001.*
Morris et al., PubMed Abstract (Invasion Metastasis, 17(6):281–96), 1997.*
Rasmussen et al., Matrix Metalloproteinase Inhibition as a Novel Anticancer Strategy, Pharmacol. Ther., vol. 75, No. 1, pp. 69–75, 1997.*
Simone, Oncology: Introduction, Cecil Textbook of Medicine, 20th Edition, vol. 1, pp. 1004–10, 1996.*
Chambers et al., Changing Views of the Role of Matrix Metalloproteinases in Mestasis, Journal of the National Cancer Institute, vol. 89, No. 17, pp. 1260–1270, 1997.*
Montana, John, et al, "The design of selective non–substrate–based matrix metalloproteinase inhibitors", Current Opinion in Drug Discovery & Development, 2000; 3(4), pp 353–361.
Clark, Ian, et al, "Matrix metalloproteinase inhibitors in the treatment of arthritis", Current Opinions in Anti–inflammatory & Immunomodulatory Investigational Drugs, 2000; 2(1), pp 16–25.
Chen, James, et al, "Structure–Based Design of a Novel, Potent, and Selective Inhibitor for MMP–13 Utilizing NMR Spectroscopy and Computer–Aided Molecular Design", J. Am. Chem. Soc., 2000, 122: pp 9648–9654.
Almstead, Neil G., et al, "Design, Synthesis, and Biological Evaluation of Potent Thiazine– and Thiazepine–Based Matrix Metalloproteinase Inhibitors", J. Med. Chem., 1999, 42; pp 4547–4562 XP–000919158.

* cited by examiner

*Primary Examiner*—Deepak Rao
(74) *Attorney, Agent, or Firm*—Charles W. Ashbrook; Claude F. Purchase, Jr.

(57) ABSTRACT

Matrix metalloproteinase inhibitors are tricyclic substituted cyclic sulfonamides of the formula

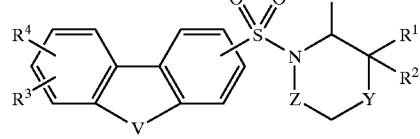

or a pharmaceutically acceptable salt thereof wherein $R^1$ and $R^2$ include hydrogen, alkyl, and substituted alkyl; $R^3$ and $R^4$ include hydrogen, halo, and alkyl; X is OH or NHOH, V is O, S, $SO_2$, $NR^5$, or $CH_2$, $R^5$ is a hydrogen or alkyl, and Z is $(CH_2)_n$, wherein n is an integer from 0 to 2.

16 Claims, No Drawings

SULFONAMIDE MATRIX METALLOPROTEINASE INHIBITORS

CROSS-REFERENCE TO RELATED APPLICATIONS

This application claims benefit of priority from U.S. provisional application No. 60/268,737, filed Feb. 14, 2001.

FIELD OF THE INVENTION

This invention relates to a group of cyclic sulfonamide compounds and derivatives that inhibit matrix metalloproteinase enzymes and thus are useful for treating diseases resulting from tissue breakdown, such as heart disease, multiple sclerosis, arthritis, atherosclerosis, and osteoporosis.

BACKGROUND OF THE INVENTION

Matrix metalloproteinases (sometimes referred to as MMPs) are naturally occurring enzymes found in most mammals. Over-expression and activation of MMPs or an imbalance between MMPs and inhibitors of MMPs have been suggested as factors in the pathogenesis of diseases characterized by the breakdown of extracellular matrix or connective tissues.

Stromelysin-1 and gelatinase A are members of the MMP family. Other members include fibroblast collagenase (MMP-1), neutrophil collagenase (MMP-8), gelatinase B (92 kDa gelatinase) (MMP-9), stromelysin-2 (MMP-10), stromelysin-3 (MMP-11), matrilysin (MMP-7), collagenase 3 (MMP-13), TNF-alpha converting enzyme (TACE), and other newly discovered membrane-associated matrix metalloproteinases (Sato H., Takino T., Okada Y., Cao J., Shinagawa A., Yamamoto E., Seiki M., *Nature,* 1994;370:61–65). These enzymes have been implicated in a number of diseases which result from breakdown of connective tissue; including such diseases as rheumatoid arthritis, osteoarthritis, osteoporosis, periodontitis, multiple sclerosis, gingivitis, corneal epidermal and gastric ulceration, atherosclerosis, neointimal proliferation which leads to restenosis and ischemic heart failure, and tumor metastasis. A method for preventing and treating these and other diseases is now recognized to be by inhibiting metalloproteinase enzymes, thereby curtailing and/or eliminating the breakdown of connective tissues that results in the disease states.

The catalytic zinc in matrix metalloproteinases is typically the focal point for inhibitor design. The modification of substrates by introducing zinc chelating groups has generated potent inhibitors such as peptide hydroxamates and thiol-containing peptides. Peptide hydroxamates and the natural endogenous inhibitors of MMPs (TIMPs) have been used successfully to treat animal models of cancer and inflammation. MMP inhibitors have also been used to prevent and treat congestive heart failure and other cardiovascular diseases. For example, see U.S. Pat. No. 5,948,780.

The need to find new low-molecular weight compounds that are potent MMP inhibitors, and that have an acceptable therapeutic index of toxicity/potency to make them amenable for clinical use in the prevention and treatment of the associated disease states, continues. An object of this invention is to provide a group of MMP inhibitors characterized as being sulfonamides bearing a tricyclic aromatic or heteroaromatic substituent.

SUMMARY OF THE INVENTION

This invention provides a group of tricyclic substituted sulfonamide compounds that are inhibitors of matrix metalloproteinase enzymes. The invention is more particularly directed to compounds defined by Formula I

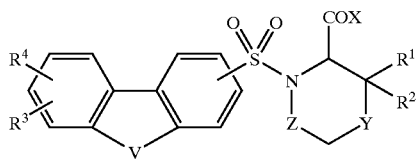

I or the pharmaceutically acceptable salts thereof wherein:

$R^1$ and $R^2$ independently are hydrogen or $C_1$–$C_6$ alkyl;

$R^3$ and $R^4$ independently are hydrogen, halo, nitro, $NR^5R^6$, $C_1$–$C_6$ alkyl, $C_2$–$C_6$ alkenyl, $C_2$–$C_6$ alkynyl; $(CH_2)_mOH$, $(CH_2)_mOR^5$, $(CH_2)_m$ cycloalkyl, $(CH_2)_m$ aryl, $(CH_2)_m$ substituted aryl, $(CH_2)_m$ heteroaryl, $(CH_2)_m$ substituted heteroaryl, $(CH_2)_m$ carbocycle, $(CH_2)_m$ heterocycle; $(CH_2)_m$ $NR^5R^6$, $(CH_2)_mCOR^5$, $(CH_2)_mCONR^5R^6$, or $(CH_2)_mCO_2R^5$;

m is an integer from 0 to 6;

$R^5$ and $R^6$ independently are hydrogen or $C_1$–$C_6$ alkyl, or taken together with the nitrogen to which they are attached complete a 3- to 7-membered ring;

Z is $(CH_2)_n$;

n is 0, 1, or 2;

Y is S, SO, or $SO_2$;

X is OH or NHOH;

V is O, S, $SO_2$, NH, $NR^5$, or $CH_2$.

Another invention embodiment is a compound of Formula II

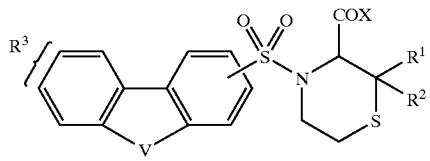

II or a pharmaceutically acceptable salt thereof, wherein $R^1$, $R^2$, $R^3$, V, and X are as defined above.

Another invention embodiment is a compound of Formula II, or a pharmaceutically acceptable salt thereof, wherein $R^3$ is halo.

Another invention embodiment is a compound of Formulas I or II, or a pharmaceutically acceptable salt thereof, wherein X is OH.

Another invention embodiment is a compound of Formulas I or II, or a pharmaceutically acceptable salt thereof, wherein X is NHOH.

Another invention embodiment is a compound of Formula III

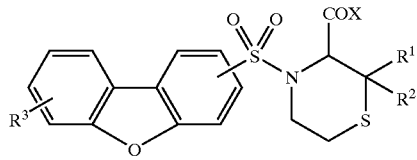

III or a pharmaceutically acceptable salt thereof, wherein $R^1$, $R^2$, $R^3$, and X are as defined above.

Another invention embodiment is a compound of Formula IV

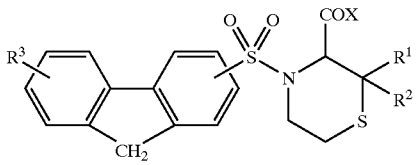

or a pharmaceutically acceptable salt thereof, wherein $R^1$, $R^2$, $R^3$, and X have the above defined meanings.

Another invention embodiment is a compound of Formula V

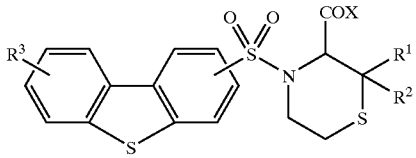

or a pharmaceutically acceptable salt thereof, wherein $R^1$, $R^2$, $R^3$, and X are as defined above.

Another invention embodiment is a compound of Formula VI

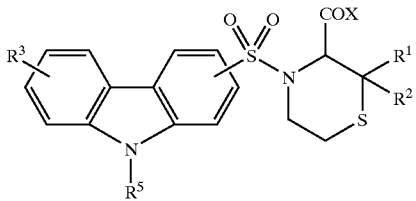

or a pharmaceutically acceptable salt thereof, wherein $R^1$, $R^2$, $R^3$, and X are as defined above.

Another invention embodiment is a compound of Formula I, or a pharmaceutically acceptable salt thereof, wherein Y is $SO_2$.

Another invention embodiment is a compound of Formula VII

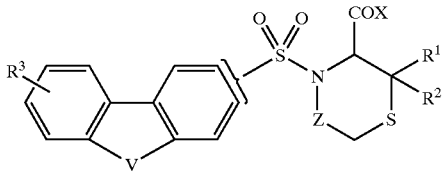

or a pharmaceutically acceptable salt thereof, wherein V, Z, X, $R^1$, and $R^2$ are as defined above for Formula I.

A further embodiment of this invention is a pharmaceutical composition, comprising a compound of Formula I, or a pharmaceutically acceptable salt thereof, admixed with a pharmaceutically acceptable carrier, excipient, or diluent.

Another invention embodiment is a pharmaceutical composition, comprising a compound of any one of Formulas II through VII, or a pharmaceutically acceptable salt thereof, admixed with a pharmaceutically acceptable carrier, excipient, or diluent.

Another invention embodiment is a pharmaceutical composition, comprising a compound selected from:

(S)-4-(Dibenzofuran-3-sulfonyl)-2,2-dimethyl-thiomorpholine-3-carboxylic acid;

(S)-4-(Dibenzofuran-3-sulfonyl)-2,2-dimethyl-thiomorpholine-3-carboxylic acid hydroxyamide;

R-3-(Dibenzofuran-3-sulfonyl)-5,5-dimethyl-thiazolidine-4-carboxylic acid;

R-3-(Dibenzofuran-3-sulfonyl)-5,5-dimethyl-thiazolidine-4-carboxylic acid hydroxyamide;

(S)-4-(9H-Fluorene-2-sulfonyl)-2,2-dimethyl-thiomorpholine-3-carboxylic acid;

(S)-4-(9H-Fluorene-2-sulfonyl)-2,2-dimethyl-thiomorpholine-3-carboxylic acid hydroxyamide;

(S)-4-(Dibenzofuran-2-sulfonyl)-2,2-dimethyl-thiomorpholine-3-carboxylic acid;

(S)-4-(Dibenzofuran-2-sulfonyl)-2,2-dimethyl-thiomorpholine-3-carboxylic acid hydroxyamide;

(S)-4-(7-Bromo-dibenzofuran-2-sulfonyl)-2,2-dimethyl-thiomorpholine-3-carboxylic acid;

(S)-4-(7-Bromo-dibenzofuran-2-sulfonyl)-2,2-dimethyl-thiomorpholine-3-carboxylic acid hydroxyamide;

(S)-4-(7-Methoxycarbonyl-dibenzofuran-2-sulfonyl)-2,2-dimethyl-thiomorpholine-3-carboxylic acid;

(S)-4-(7-Methoxycarbonyl-dibenzofuran-2-sulfonyl)-2,2-dimethyl-thiomorpholine-3-carboxylic acid hydroxyamide;

(S)-2,2-Dimethyl-4-(7-nitro-dibenzofuran-2-sulfonyl)-thiomorpholine-3-carboxylic acid;

(S)-2,2-Dimethyl-4-(7-nitro-dibenzofuran-2-sulfonyl)-thiomorpholine-3-carboxylic acid hydroxyamide;

(S)-4-(Dibenzofuran-2-sulfonyl)-2,2-dimethyl-1,1-dioxo-thiomorpholine-3-carboxylic acid hydroxyamide;

(S)-4-(7-Isobutyrylamino-dibenzofuran-2-sulfonyl)-2,2-dimethyl-thiomorpholine-3-carboxylic acid;

(S)-2,2-Dimethyl-4-[7-(3-phenyl-propionylamino)-dibenzofuran-2-sulfonyl]-thiomorpholine-3-carboxylic acid;

(S)-2,2-Dimethyl-4-[7-(4-methyl-pentanoylamino)-dibenzofuran-2-sulfonyl]-thiomorpholine-3-carboxylic acid;

(S)-4-(7-Benzoylamino-dibenzofuran-2-sulfonyl)-2,2-dimethyl-thiomorpholine-3-carboxylic acid;

(S)-2,2-Dimethyl-4-(7-propionylamino-dibenzofuran-2-sulfonyl)-thiomorpholine-3-carboxylic acid;

(S)-4-[7-(3-Ethyl-ureido)-dibenzofuran-2-sulfonyl]-2,2-dimethyl-thiomorpholine-3-carboxylic acid;

(S)-4-[7-(3-Isopropyl-ureido)-dibenzofuran-2-sulfonyl]-2,2-dimethyl-thiomorpholine-3-carboxylic acid;

(S)-2,2-Dimethyl-4-[7-(3-phenyl-ureido)-dibenzofuran-2-sulfonyl]-2,2-dimethyl-thiomorpholine-3-carboxylic acid;

(S)-4-[7-(3,3-Diethyl-ureido)-dibenzofuran-2-sulfonyl]-2,2-dimethyl-thiomorpholine-3-carboxylic acid;

(S)-4-[7-(2,4-Dichloro-benzoylamino)-dibenzofuran-2-sulfonyl]-2,2-dimethyl-thiomorpholine-3-carbxoylic acid hydroxyamide;

(S)-4-[7-(3,4-Dimethoxy-benzoylamino)-dibenzofuran-2-sulfonyl]-2,2-dimethyl-thiomorpholine-3-carboxylic acid hydroxyamide;

(S)-4-[7-(2,5-Dimethoxy-benzoylamino)-dibenzofuran-2-sulfonyl]-2,2-dimethyl-thiomorpholine-3-carboxylic acid hydroxyamide;

(S)-2,2-Dimethyl-4-(7-phenylacetylamino-dibenzofuran-2-sulfonyl)-thiomorpholine-3-carboxylic acid hydroxyamide;

(S)-2,2-Dimethyl-4-{7-[(thiophene-2-carbonyl)-amino]-dibenzofuran-2-sulfonyl}-thiomorpholine-3-carboxylic acid hydroxyamide;

(S)-4-[7-(3-Ethyl-ureido)-dibenzofuran-2-sulfonyl]-2,2-dimethyl-thiomorpholine-3-carboxylic acid hydroxyamide;

(S)-4-[7-(3-Isopropyl-ureido)-dibenzofuran-2-sulfonyl]-2,2-dimethyl-thiomorpholine-3-carboxylic acid hydroxyamide;

(S)-2,2-Dimethyl-4-[7-(3-phenyl-ureido)-dibenzofuran-2-sulfonyl]-2,2-dimethyl-thiomorpholine-3-carboxylic acid hydroxyamide;

(S)-4-[7-(3,3-Diethyl-ureido)-dibenzofuran-2-sulfonyl]-2,2-dimethyl-thiomorpholine-3-carboxylic acid hydroxyamide;

2,2-Dimethyl-4-[7-(3-nitro-benzoylamino)-dibenzofuran-2-sulfonyl]-thiomorpholine-3-carboxylic acid hydroxyamide;

4-(7-Dodecanoylamino-dibenzofuran-2-sulfonyl)-2,2-dimethyl-thiomorpholine-3-carboxylic acid hydroxyamide;

N-[8-(3-Hydroxycarbamoyl-2,2-dimethyl-thiomorpholine-4-sulfonyl)-dibenzofuran-3-yl]-oxalamic acid ethyl ester;

4-[7-(Cyclohexanecarbonyl-amino)-dibenzofuran-2-sulfonyl]-2,2-dimethyl-thiomorpholine-3-carboxylic acid hydroxyamide;

4-[7-(2-Fluoro-benzoylamino)-dibenzofuran-2-sulfonyl]-2,2-dimethyl-thiomorpholine-3-carboxylic acid hydroxyamide;

4-(7-Acetylamino-dibenzofuran-2-sulfonyl)-2,2-dimethyl-thiomorpholine-3-carboxylic acid hydroxyamide;

Acetic acid 2-[8-(3-hydroxycarbamoyl-2,2-dimethyl-thiomorpholine-4-sulfonyl)-dibenzofuran-3-ylcarbamoyl]-phenyl ester;

4-(7-Benzoylamino-dibenzofuran-2-sulfonyl)-2,2-dimethyl-thiomorpholine-3-carboxylic acid hydroxyamide;

4-(7-Butyrylamino-dibenzofuran-2-sulfonyl)-2,2-dimethyl-thiomorpholine-3-carboxylic acid hydroxyamide;

4-(7-Decanoylamino-dibenzofuran-2-sulfonyl)-2,2-dimethyl-thiomorpholine-3-carboxylic acid hydroxyamide;

4-(7-Decanoylamino-dibenzofuran-2-sulfonyl)-2,2-dimethyl-thiomorpholine-3-carboxylic acid hydroxyamide;

4-(7-Diphenylacetylamino-dibenzofuran-2-sulfonyl)-2,2-dimethyl-thiomorpholine-3-carboxylic acid hydroxyamide;

4-{7-[2-(4-Chloro-phenoxy)-acetylamino]-dibenzofuran-2-sulfonyl}-2,2-dimethyl-thiomorpholine-3-carboxylic acid hydroxyamide;

N-[8-(3-Hydroxycarbamoyl-2,2-dimethyl-thiomorpholine-4-sulfonyl)-dibenzofuran-3-yl]-succinamic acid methyl ester;

4-[7-(3,4-Dimethoxy-benzoylamino)-dibenzofuran-2-sulfonyl]-2,2-dimethyl-thiomorpholine-3-carboxylic acid hydroxyamide;

4-[7-(2-Methoxy-benzoylamino)-dibenzofuran-2-sulfonyl]-2,2-dimethyl-thiomorpholine-3-carboxylic acid hydroxyamide;

4-[7-(2,2-Dimethyl-pentanoylamino)-dibenzofuran-2-sulfonyl]-2,2-dimethyl-thiomorpholine-3-carboxylic acid hydroxyamide;

4-[7-(2,4-Dichloro-benzoylamino)-dibenzofuran-2-sulfonyl]-2,2-dimethyl-thiomorpholine-3-carboxylic acid hydroxyamide;

4-[7-(2,5-Dimethoxy-benzoylamino)-dibenzofuran-2-sulfonyl]-2,2-dimethyl-thiomorpholine-3-carboxylic acid hydroxyamide;

2,2-Dimethyl-4-[7-(4-methyl-pentanoylamino)-dibenzofuran-2-sulfonyl]-thiomorpholine-3-carboxylic acid hydroxyamide;

4-[7-(Cyclopropanecarbonyl-amino)-dibenzofuran-2-sulfonyl]-2,2-dimethyl-thiomorpholine-3-carboxylic acid hydroxyamide;

Acetic acid [8-(3-hydroxycarbamoyl-2,2-dimethyl-thiomorpholine-4-sulfonyl)-dibenzofuran-3-ylcarbamoyl]-phenyl-methyl ester;

2,2-Dimethyl-4-{7-[(tricyclo[3.3.1]decanane-1-carbonyl)-amino]-dibenzofuran-2-sulfonyl}-thiomorpholine-3-carboxylic acid hydroxyamide;

2,2-Dimethyl-4-(7-pentanoylamino-dibenzofuran-2-sulfonyl)-thiomorpholine-3-carboxylic acid hydroxyamide;

4-[7-(2,2-Dimethyl-propionylamino)-dibenzofuran-2-sulfonyl]-2,2-dimethyl-thiomorpholine-3-carboxylic acid hydroxyamide;

2,2-Dimethyl-4-[7-((Z)-octadec-9-enoylamino)-dibenzofuran-2-sulfonyl]-thiomorpholine-3-carboxylic acid hydroxyamide;

N-[8-(3-Hydroxycarbamoyl-2,2-dimethyl-thiomorpholine-4-sulfonyl)-dibenzofuran-3-yl]-succinamic acid ethyl ester;

4-(7-Isobutyrylamino-dibenzofuran-2-sulfonyl)-2,2-dimethyl-thiomorpholine-3-carboxylic acid hydroxyamide;

4-(7-Isobutyrylamino-dibenzofuran-2-sulfonyl)-2,2-dimethyl-thiomorpholine-3-carboxylic acid hydroxyamide;

4-[7-(3-Chloro-benzoylamino)-dibenzofuran-2-sulfonyl]-2,2-dimethyl-thiomorpholine-3-carboxylic acid hydroxyamide;

2,2-Dimethyl-4-(7-nonanoylamino-dibenzofuran-2-sulfonyl)-thiomorpholine-3-carboxylic acid hydroxyamide;

2,2-Dimethyl-4-[7-(2-trifluoromethyl-benzoylamino)-dibenzofuran-2-sulfonyl]-thiomorpholine-3-carboxylic acid hydroxyamide;

2,2-Dimethyl-4-[7-(2-trifluoromethyl-benzoylamino)-dibenzofuran-2-sulfonyl]-thiomorpholine-3-carboxylic acid hydroxyamide;

2,2-Dimethyl-4-(7-octanoylamino-dibenzofuran-2-sulfonyl)-thiomorpholine-3-carboxylic acid hydroxyamide;

4-(7-Hexadecanoylamino-dibenzofuran-2-sulfonyl)-2,2-dimethyl-thiomorpholine-3-carboxylic acid hydroxyamide;

4-(7-Hexadecanoylamino-dibenzofuran-2-sulfonyl)-2,2-dimethyl-thiomorpholine-3-carboxylic acid hydroxyamide;

2,2-Dimethyl-4-[7-(2,2,3,3,4,4,5,5,6,6,7,7,8,8,8-pentadecafluoro-octanoylamino)-dibenzofuran-2-sulfonyl]-thiomorpholine-3-carboxylic acid hydroxyamide;

2,2-Dimethyl-4-[7-(2-phenoxy-acetylamino)-dibenzofuran-2-sulfonyl]-thiomorpholine-3-carboxylic acid hydroxyamide;

2,2-Dimethyl-4-[7-(2-phenoxy-acetylamino)-dibenzofuran-2-sulfonyl]-thiomorpholine-3-carboxylic acid hydroxyamide;

2,2-Dimethyl-4-(7-phenylacetylamino-dibenzofuran-2-sulfonyl)-thiomorpholine-3-carboxylic acid hydroxyamide;

2,2-Dimethyl-4-(7-propionylamino-dibenzofuran-2-sulfonyl)-thiomorpholine-3-carboxylic acid hydroxyamide;

2,2-Dimethyl-4-(7-tridecanoylamino-dibenzofuran-2-sulfonyl)-thiomorpholine-3-carboxylic acid hydroxyamide;

4-[7-(3,5-Dinitro-benzoylamino)-dibenzofuran-2-sulfonyl]-2,2-dimethyl-thiomorpholine-3-carboxylic acid hydroxyamide;

N-[8-(3-Hydroxycarbamoyl-2,2-dimethyl-thiomorpholine-4-sulfonyl)-dibenzofuran-3-yl]-malonamic acid ethyl ester;

N-[8-(3-Hydroxycarbamoyl-2,2-dimethyl-thiomorpholine-4-sulfonyl)-dibenzofuran-3-yl]-malonamic acid ethyl ester;

2,2-Dimethyl-4-[7-(2,2,2-trichloro-acetylamino)-dibenzofuran-2-sulfonyl]-thiomorpholine-3-carboxylic acid hydroxyamide;

2,2-Dimethyl-4-{7-[(thiophene-2-carbonyl)-amino]-dibenzofuran-2-sulfonyl}-thiomorpholine-3-carboxylic acid hydroxyamide;

2,2-Dimethyl-4-[7-(3-phenyl-propionylamino)-dibenzofuran-2-sulfonyl]-thiomorpholine-3-carboxylic acid hydroxyamide; and 4-[7-(2-Bromo-benzoylamino)-dibenzofuran-2-sulfonyl]-2,2-dimethyl-thiomorpholine-3-carboxylic acid hydroxyamide, or a pharmaceutically acceptable salt thereof, admixed with a pharmaceutically acceptable carrier, diluent, or excipient.

Another embodiment of this invention is a method for inhibiting MMP enzymes in an animal, comprising administering to the animal an MMP inhibiting amount of a compound of Formula I, or a pharmaceutically acceptable salt thereof.

A further embodiment is a method for treating a disease mediated by an MMP enzyme, comprising administering to a patient suffering from such disease an effective amount of a compound of Formula I, or a pharmaceutically acceptable salt thereof.

Another invention embodiment is a method for treating a cancer, comprising administering to a patient suffering from such a disease an anticancer effective amount of a compound of Formula I, or a pharmaceutically acceptable salt thereof.

Another invention embodiment is a method for treating breast carcinoma, comprising administering to a patient suffering from such a disease an anticancer effective amount of a compound of Formula I, or a pharmaceutically acceptable salt thereof.

Another invention embodiment is a method for treating a rheumatoid arthritis, comprising administering to a patient suffering from such a disease an effective amount of a compound of Formula I, or a pharmaceutically acceptable salt thereof.

Another invention embodiment is a method for treating a osteoarthritis, comprising administering to a patient suffering from such a disease an effective amount of a compound of Formula I, or a pharmaceutically acceptable salt thereof.

Another invention embodiment is a method for treating a heart failure, comprising administering to a patient suffering from such a disease an effective amount of a compound of Formula I, or a pharmaceutically acceptable salt thereof.

Another invention embodiment is a method for treating a inflammation, comprising administering to a patient suffering from such a disease an effective amount of a compound of Formula I, or a pharmaceutically acceptable salt thereof.

Another embodiment of this invention is use of a compound of claim 1, or a pharmaceutically acceptable salt thereof, in the manufacture of a medicament for the treatment of a disease mediated by an MMP enzyme.

Another invention embodiment is use of a compound of claim 1, or a pharmaceutically acceptable salt thereof, in the manufacture of a medicament for the treatment of cancer.

Another invention embodiment is use of a compound of claim 1, or a pharmaceutically acceptable salt thereof, in the manufacture of a medicament for the treatment of arthritis.

Another invention embodiment is use of a compound of claim 1, or a pharmaceutically acceptable salt thereof, in the manufacture of a medicament for the treatment of rheumatoid arthritis.

Another invention embodiment is use of a compound of claim 1, or a pharmaceutically acceptable salt thereof, in the manufacture of a medicament for the treatment of osteoarthritis.

Another invention embodiment is use of a compound of claim 1, or a pharmaceutically acceptable salt thereof, in the manufacture of a medicament for the treatment of congestive heart failure.

DETAILED DESCRIPTION OF THE INVENTION

The compounds provided by this invention are those defined by Formula I. In Formula I, $R^1$–$R^4$ include "$C_1$–$C_6$ alkyl" groups. These are straight and branched carbon chains having from 1 to 6 carbon atoms. Examples of such alkyl groups include methyl, ethyl, isopropyl, tert.-butyl, neopentyl, and n-hexyl. The alkyl groups can be substituted if desired, for instance with groups such as hydroxy, amino, alkyl, and dialkylamino, halo, trifluoromethyl, carboxy, nitro, and cyano.

"Halo" includes fluoro, chloro, bromo, and iodo.

"Alkenyl" means straight and branched hydrocarbon radicals having from 2 to 6 carbon atoms and one double bond and includes ethenyl, 3-buten-1-yl, 2-ethenylbutyl, 3-hexen-1-yl, and the like.

"Alkynyl" means straight and branched hydrocarbon radicals having from 2 to 6 carbon atoms and 1 triple bond and includes ethynyl, 3-butyn-1-yl, propynyl, 2-butyn-1-yl, 3-pentyn-1-yl, and the like.

"Cycloalkyl" means a monocyclic or polycyclic hydrocarbyl group such as cyclopropyl, cycloheptyl, cyclooctyl, cyclodecyl, cyclobutyl, adamantyl, norpinanyl, decalinyl, norbornyl, cyclohexyl, and cyclopentyl. Such groups can be substituted with groups such as hydroxy, keto, and the like. Also included are rings in which 1 to 3 heteroatoms replace carbons. Such groups are termed "heterocyclyl", which means a cycloalkyl group also bearing at least one heteroatom selected from O, S, or $NR^2$, examples being oxiranyl, pyrrolidinyl, piperidyl, tetrahydropyran, and morpholine.

"Alkoxy" refers to the alkyl groups mentioned above bound through oxygen, examples of which include methoxy, ethoxy, isopropoxy, tert-butoxy, and the like. In addition, alkoxy refers to polyethers such as —O—$(CH_2)_2$—O—$OH_3$, and the like.

"Alkanoyl" groups are alkyl linked through a carbonyl, i.e., $C_1$–$C_5$—C(O)—. Such groups include formyl, acetyl, propionyl, butyryl, and isobutyryl.

"Acyl" means an alkyl or aryl (Ar) group bonded through a carbonyl group, i.e., R—C(O)—, where R is alkyl, aryl, heteroaryl, arylalkyl, heteroarylalkyl, all optionally substituted. For example, acyl includes a $C_1$–$C_6$ alkanoyl, including substituted alkanoyl, wherein the alkyl portion can be substituted by $NR^5R^6$ or a carboxylic or heterocyclic group. Typical acyl groups include acetyl, benzoyl, and the like.

The alkyl, alkenyl, alkoxy, and alkynyl groups described above are optionally substituted, preferably by 1 to 3 groups selected from $NR^5R^6$, phenyl, substituted phenyl, thio $C_1$–$C_6$ alkyl, $C_1$–$C_6$ alkoxy, hydroxy, carboxy, $C_1$–$C_6$ alkoxycarbonyl, halo, nitrile, cycloalkyl, and a 5- or 6-membered carbocyclic ring or heterocyclic ring having 1 or 2 heteroatoms selected from nitrogen, substituted nitrogen, oxygen, and sulfur. "Substituted nitrogen" means nitrogen bearing $C_1$–$C_6$ alkyl or $(CH_2)_n$Ph where n is 1, 2, or 3. Perhalo and polyhalo substitution is also embraced.

Examples of substituted alkyl groups include 2-aminoethyl, pentachloroethyl, trifluoromethyl, 2-diethylaminoethyl, 2-dimethylaminopropyl, ethoxycarbonylmethyl, 3-phenylbutyl, methanylsulfanylmethyl, methoxymethyl, 3-hydroxypentyl, 2-carboxybutyl, 4-chlorobutyl, 3-cyclopropylpropyl, pentafluoroethyl, 3-morpholinopropyl, piperazinylmethyl, and 2-(4-methylpiperazinyl)ethyl.

Examples of substituted alkynyl groups include 2-methoxyethynyl, 2-ethylsulfanyethynyl, 4-(1-piperazinyl)-3-(butynyl), 3-phenyl-5-hexynyl, 3-diethylamino-3-butynyl, 4-chloro-3-butynyl, 4-cyclobutyl-4-hexenyl, and the like.

Typical substituted alkoxy groups include aminomethoxy, trifluoromethoxy, 2-diethylaminoethoxy, 2-ethoxycarbonylethoxy, 3-hydroxypropoxy, 6-carboxyhexyloxy, and the like.

Further, examples of substituted alkyl, alkenyl, and alkynyl groups include dimethylaminomethyl, carboxymethyl, 4-dimethylamino-3-buten-1-yl, 5-ethylmethylamino-3-pentyn-1-yl, 4-morpholinobutyl, 4-tetrahydropyrinidylbutyl, 3-imidazolidin-1-ylpropyl, 4-tetrahydrothiazol-3-yl-butyl, phenylmethyl, 3-chlorophenylmethyl, and the like.

As noted above, $R^4$ and $R^5$ include hydrogen, alkyl, and aryl. Examples of $NR^4R^5$ groups include amino, methylamino, di-isopropylamino, acetyl amino, propionyl amino, 3-aminopropyl amino, 3-ethylaminobutyl amino, 3-di-n-propylamino-propyl amino, 4-diethylaminobutyl amino, and 3-carboxypropionyl amino. $R^4$ and $R^5$ can be taken together with the nitrogen to which they are attached to form a ring having 3 to 7 carbon atoms and 1, 2, or 3 heteroatoms selected from the group consisting of nitrogen, substituted nitrogen, oxygen, and sulfur. Examples of such cyclic $NR^4R^5$ groups include pyrrolidinyl, piperazinyl, 4-methylpiperazinyl, 4-benzylpiperazinyl, pyridinyl, piperidinyl, pyrazinyl, morpholinyl, and the like.

The terms "Ar" and "aryl" refer to unsubstituted and substituted aromatic groups. Heteroaryl groups have from 4 to 9 ring atoms, from 1 to 4 of which are independently selected from the group consisting of O, S, and N. Preferred heteroaryl groups have 1 or 2 heteroatoms in a 5- or 6-membered aromatic ring. Mono- and bicyclic aromatic ring systems are included in the definition of aryl and heteroaryl. Typical aryl and heteroaryl groups include phenyl, 3-chlorophenyl, 2,6-dibromophenyl, pyridyl, 3-methylpyridyl, benzothienyl, 2,4,6-tribromophenyl, 4-ethylbenzothienyl, furanyl, 3,4-diethylfuranyl, naphthyl, 4,7-dichloronaphthyl, morpholinyl, indolyl, benzotriazolyl, indazolyl, pyrrole, pyrazole, imidazole, thiazole, and the like.

Preferred Ar groups are phenyl and phenyl substituted by 1, 2, or 3 groups independently selected from the group consisting of alkyl, alkoxy, thio, thioalkyl, halo, hydroxy, —$COOR^7$, trifluoromethyl, nitro, amino of the formula —$NR^5R^6$, and $T(CH_2)_mQR^5$ or $T(CH_2)_mCO_2R^5$ wherein m is 1 to 6, T is O, S, $NR^5$, $N(O)R^5$, $NR^5R^6Z$, or $CR^5R^6$, Q is O, S, $NR^5$, $N(O)R^5$, or $NR^4R^5R^6Y$ wherein $R^4$, $R^5$, and $R^6$ are as described above, $R^7$ is alkyl or substituted alkyl, for example, methyl, trichloroethyl, diphenylmethyl, and the like, and Z is a counter ion such as chloride or bromide. The alkyl and alkoxy groups can be substituted as defined above. For example, typical groups are carboxyalkyl, alkoxycarbonylalkyl, hydroxyalkyl, hydroxyalkoxy, and alkoxyalkyl.

The term "patient" means a mammal. Preferred patients include humans, cats, dogs, cows, horses, pigs, and sheep.

The term "animal" means a mammal. Preferred animals include humans, rats, mice, guinea pigs, rabbits, monkeys, cats, dogs, cows, horses, pigs, and sheep.

The phrases "therapeutically effective amount" and "effective amount" are synonymous unless otherwise indicated, and mean an amount of a compound of the present invention that is sufficient to improve the condition, disease, or disorder being treated. Determination of a therapeutically effective amount, as well as other factors related to effective administration of a compound of the present invention to a patient in need of treatment, including dosage forms, routes of administration, and frequency of dosing, may depend upon the particulars of the condition that is encountered, including the patient and condition being treated, the severity of the condition in a particular patient, the particular compound being employed, the particular route of administration being employed, the frequency of dosing, and the particular formulation being employed. Determination of a therapeutically effective treatment regimen for a patient is within the level of ordinary skill in the medical or veterinarian arts. In clinical use, an effective amount may be the amount that is recommended by the United States Food and Drug Administration, or an equivalent foreign agency.

The phrase "admixed" or "in admixture" means the ingredients so mixed comprise either a heterogeneous or homogeneous mixture. Preferred is a homogeneous mixture.

The phrases "pharmaceutical preparation" and "preparation" are synonymous unless otherwise indicated, and include the formulation of the active compound with encapsulating material as a carrier providing a capsule in which the active component, with or without other carriers, is surrounded by a carrier, which is thus in association with it. Similarly, cachets and lozenges are included. Pharmaceutical preparations are fully described below.

The phrase "anticancer effective amount" means an amount of invention compound, or a pharmaceutically acceptable salt thereof, sufficient to inhibit, halt, or cause regression of the cancer being treated in a particular patient or patient population. For example in humans or other mammals, an anticancer effective amount can be determined experimentally in a laboratory or clinical setting, or may be the amount required by the guidelines of the United States Food and Drug Administration, or equivalent foreign agency, for the particular cancer and patient being treated.

The phrase "MMP-13 inhibiting amount" means an amount of invention compound, or a pharmaceutically acceptable salt thereof, sufficient to inhibit an enzyme matrix metalloproteinase-13, including a truncated form thereof, including a catalytic domain thereof, in a particular animal or animal population. For example in a human or other mammal, an MMP-13 inhibiting amount can be determined experimentally in a laboratory or clinical setting, or may be the amount required by the guidelines of the United States Food and Drug Administration, or equivalent foreign agency, for the particular MMP-13 enzyme and patient being treated.

It should be appreciated that the matrix metalloproteinases include the following enzymes:

MMP-1, also known as interstitial collagenase, collagenase-1, or fibroblast-type collagenase;

MMP-2, also known as gelatinase A or 72 kDa Type IV collagenase;

MMP-3, also known as stromelysin or stromelysin-1;

MMP-7, also known as matrilysin or PUMP-1;

MMP-8, also known as collagenase-2, neutrophil collagenase, or polymorphonuclear-type ("PMN-type") collagenase;

MMP-9, also known as gelatinase B or 92 kDa Type IV collagenase;

MMP-10, also known as stromelysin-2;

MMP-11, also known as stromelysin-3;

MMP-12, also known as metalloelastase;

MMP-13, also known as collagenase-3;

MMP-14, also known as membrane-type ("MT") 1-MMP or MT1-MMP;

MMP-15, also known as MT2-MMP;

MMP-16, also known as MT3-MMP;

MMP-17, also known as MT4-MMP;

MMP-18; and

MMP-19.

Other MMPs are known, including MMP-26, which is also known as matrilysin-2.

The term "$IC_{50}$" means the concentration of test compound required to inhibit activity of a biological target, such as a receptor or enzyme, by 50%.

The phrase "a method for inhibiting MMP enzymes" includes methods of inhibiting full-length MMP enzymes, truncated forms thereof that retain catalytic activity, including forms that contain the catalytic domains of the MMP enzymes, as well as the catalytic domains of the MMP enzymes alone, and truncated forms of the catalytic domains that retain at least some catalytic activity.

It should be appreciated that it has been shown previously (Ye Qi-Zhuang, et al., supra, 1996) that inhibitor activity against a catalytic domain of an MMP is predictive of the inhibitor activity against the respective full-length enzyme.

The compounds to be used in the present invention can exist in unsolvated forms as well as solvated forms, including hydrated forms. In general, the solvated forms, including hydrated forms, are equivalent to unsolvated forms and are intended to be encompassed within the scope of the present invention. Several of the compounds have one or more chiral centers, and as such can exist as racemates and pure enantiomers. All optical isomers and positional isomers are included in the scope of this invention.

The compounds of Formulas I through VII are capable of further forming both pharmaceutically acceptable salts, including but not limited to acid addition and/or base salts, solvents and N-oxides of a compound of Formulas I through VII. This invention also provides pharmaceutical formulations comprising a compound of Formulas I through VII together with a pharmaceutically acceptable carrier, diluent, or excipient therefor. All of these forms can be used in the method of the present invention.

Pharmaceutically acceptable acid addition salts of the compounds of Formulas I through VII include salts derived form inorganic acids such as hydrochloric, nitric, phosphoric, sulfuric, hydrobromic, hydroiodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are the salts of amino acids such as arginate, gluconate, galacturonate, and the like; see, for example, Berge et al., "Pharmaceutical Salts," *J. of Pharmaceutical Science*, 1977;66:1–19.

The acid addition salts of the basic compounds are prepared by contacting the free-base form with a sufficient amount of the desired acid to produce the salt in the conventional manner. The free-base form may be regenerated by contacting the salt form with a base and isolating the free base in the conventional manner. The free-base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine. For example, see Berge et al., supra, 1977.

The base addition salts of acidic compounds are prepared by contacting the free-acid form with a sufficient amount of the desired base to produce the salt in the conventional manner. The free-acid form may be regenerated by contacting the salt form with an acid and isolating the free acid in a conventional manner. The free-acid forms differ from their respective salt forms somewhat in certain physical properties such as solubility in polar solvents, but otherwise the salts are equivalent to their respective free acid for purposes of the present invention.

The compounds of the present invention can be formulated and administered in a wide variety of oral and parenteral dosage forms, including transdermal and rectal administration. All that is required is that an MMP inhibitor be administered to a mammal suffering from a disease in an effective amount, which is that amount required to cause an improvement in the disease and/or the symptoms associated with such disease. It will be recognized by those skilled in the art that the following dosage forms may comprise as the active component, either a compound of Formulas I through VII, or a corresponding pharmaceutically acceptable salt or solvate of a compound of Formulas I through VII.

A compound of Formula I, or a pharmaceutically acceptable salt thereof, may be prepared by one of ordinary skill in the art of organic chemistry by procedures found in the chemical literature such as, for example, *Reagents for Organic Synthesis* by Fieser and Fieser, New York: 2000, John Wiley & Sons, Inc.; *Comprehensive Organic Transformations*, by Richard C. Larock, VCH Publishers, Inc., New York, 1989; the series *Compendium of Organic Synthetic Methods* by Wiley-Interscience, 1989; the text *Advanced Organic Chemistry*, $5^{th}$ edition, by Jerry March, New York: 2001, Wiley-Interscience; or the *Handbook of Heterocyclic Chemistry*, by Alan R. Katritzky, London: Pergamon Press Ltd, 1985, to name a few. Alternatively, a skilled artisan may find methods useful for preparing the invention compounds in the chemical literature by searching widely available databases such as, for example, those available from the *Chemical Abstracts Service*, Columbus, Ohio, or *MDL Information Systems GmbH* (formerly *Beilstein Information Systems GmbH*), Frankfurt, Germany.

Preparations of the compounds of the present invention may use starting materials, reagents, solvents, and catalysts that may be purchased from commercial sources or they may be readily prepared by adapting procedures in the references or resources cited above. Commercial sources of starting materials, reagents, solvents, and catalysts useful in preparing invention compounds include, for example, *The Aldrich Chemical Company*, and other subsidiaries of Sigma-Aldrich Corporation, St. Louis, Mo., *BACHEM*, BACHEM A.G., Switzerland, or *Lancaster Synthesis Ltd*, United Kingdom.

*Reagents for Organic Synthesis*, by Fieser and Fieser, New York, John Wiley & Sons, Inc., 2000; *Comprehensive Organic Transformations*, by Richard C. Larock, VCH Publishers, Inc., New York, 1989; the series *Compendium of*

*Organic Synthetic Methods* by Wiley-Interscience, 1989; the text *Advanced Organic Chemistry*, 5th edition, by Jerry March, Wiley-Interscience, New York 2001; and the *Handbook of Heterocyclic Chemistry*, by Alan R. Katritzky, Pergamon Press Ltd., London, 1985 are hereby incorporated by reference.

The compounds of the invention are prepared by methods well known to those skilled in the art of organic chemistry. The compounds of Formula I are prepared utilizing commercially available starting materials, or reactants that are readily prepared by standard organic synthetic techniques. A typical synthesis of the invention compounds of Formula I is shown in Scheme 1 below. The first step in Scheme 1 comprises reacting a tricyclic aromatic or heteroaromatic sulfonyl chloride (1) with a substituted thiomorpholine carboxylic acid ester (2). These reactants are generally combined in approximately equimolar quantities in a mutual organic solvent such as dichloromethane, and in the presence of an acid scavenger such as triethylamine. Generally, the reaction is substantially complete within about 2 to 8 hours when carried out at a temperature of about 20° C. to 60° C. The product, a sulfonamide ester of Formula I (3), can be isolated if desired by removing the reaction solvent by evaporation; and can be purified if desired by recrystallization from solvents such as ethyl acetate and hexane. The sulfonamide ester (3) is next hydrolyzed by reaction with a strong acid such as trifluoroacetic acid, generally in the presence of a free radical scavenger. such as anisole. The sulfonamide acid (4) is generally isolated by simply removing the reaction solvent, and it can be crystallized or chromatographed if desired. The sulfonamide carboxylic (4, where X is OH) acid can be converted to the hydroxamic acid (5, where X is NHOH) by reaction with oxalyl chloride to form the corresponding acid chloride in situ, and then reaction with excess hydroxylamine in the presence of a base such as sodium bicarbonate.

The thiomorpholines of Formula I wherein Y is S are readily converted to the corresponding sulfoxides and sulfones (where Y is SO and SO2) by oxidation with a peracid such as peracetic acetic acid or metachloroperbenzoic acid. This is shown in Scheme 1 (5 to 5).

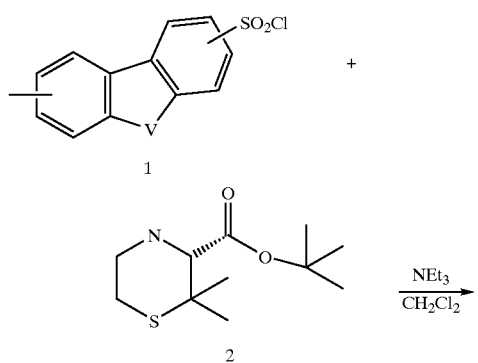

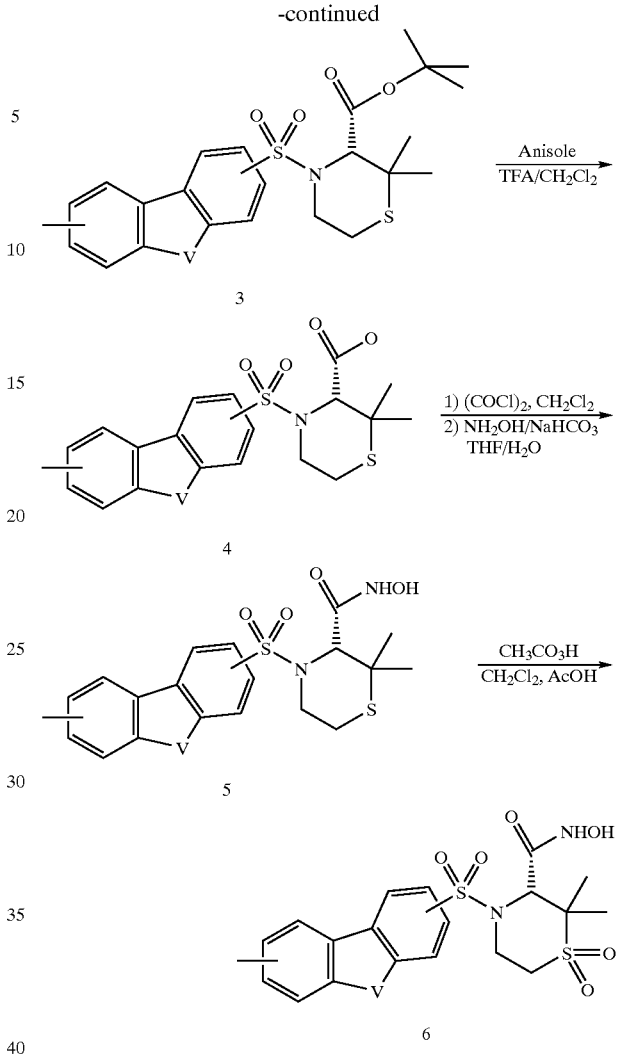

The invention compounds of Formula I are ideally suited to synthesis by general combinatorial methodologies. Schemes 2 and 3 illustrate the use of resin supports to facilitate the rapid synthesis of invention compounds. As shown in Scheme 2, a tricyclic-thiomorpholine carboxylic acid (4) is reacted with an acylating agent such as a benzoyl halide to form a mixed anhydride, which is then reacted in situ with a solid resin (e.g., a polystyrene resin "PS" such as a commercially available Wang resin) through the oxygen atom to provide a tricyclic-thiomorpholine carboxylic acid bound to a resin support (compound 8 in Scheme 2). Functional groups at other sites in the molecule (e.g., $R^3$ and $R^4$) can be modified by standard methods to provide invention compounds. For example, when $R^3$ of Formula I compounds is a nitro group, it is readily reduced by reaction with a standard reducing agent such as tin chloride to provide the corresponding amino analog (8). The amino group can be acylated by reaction with a common acylating agent such as an acid chloride to give an N-aryl analog of Formula I (a). Alternatively, the amino group can be reacted with an isocyanate RNCO to give ureas of Formula I (10). The tricyclic-thiomorpholine carboxylic acid is readily liberated from the Wang resin by reaction with a strong acid such as trifluoroacetic acid (to give 9 or 10).

Scheme 2

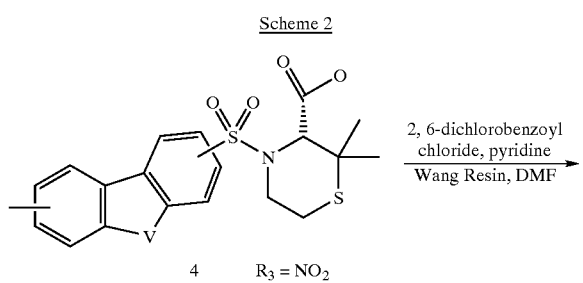

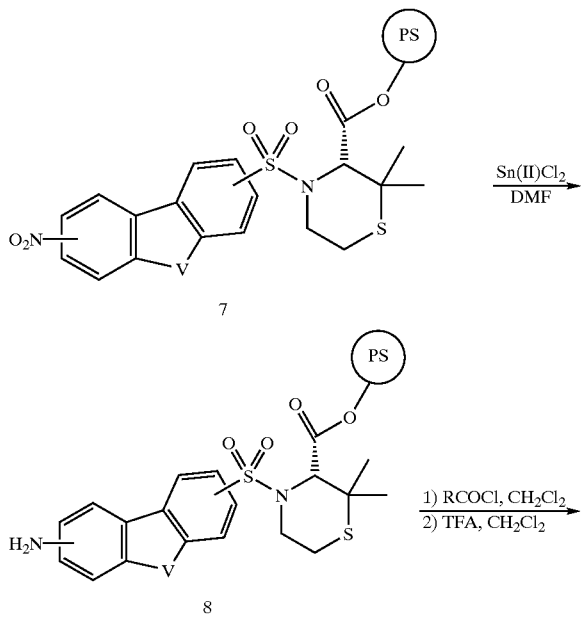

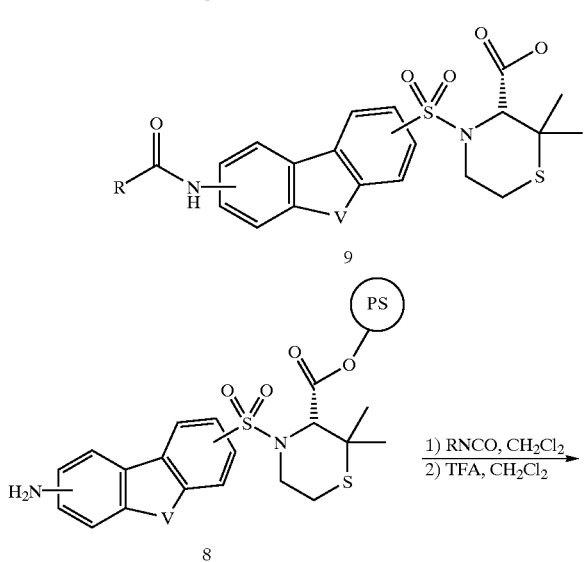

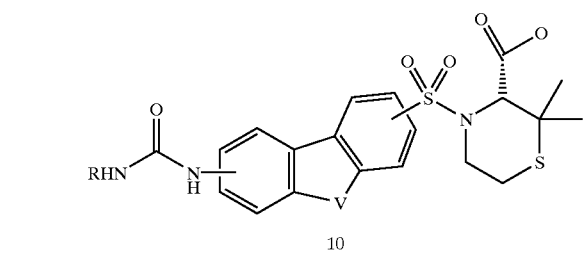

Scheme 3 illustrates the use of a hydroxylamine resin to prepare hydroxamic acids of Formula I (X=NHOH). A tricyclic-thiomorpholine carboxylic acid (4 where X=OH) is first activated at the carboxy group by reaction with a peptide coupling reagent such as dicyclohexylcarbodiimide (DCC) or 1,3-diisopropylcarbodiimide. The activated tricyclic-thiomorpholine carboxylic acid is then reacted with a hydroxylamine resin, generally in the presence of a base such as 4-dimethylaminopyridine (DMAP), to form the resin-bound hydroxamic acid analog (11). Modifications at other sites in the molecule can be carried out as described above in Scheme 2 (nitro groups reduced to amino groups, amino groups alkylated or acylated, etc). Following such modifications, the tricyclic-thiomorpholine hydroxamic acid is readily liberated from the resin by simple acid hydrolysis, for example by reaction with trifluoroacetic acid or the like.

Scheme 3

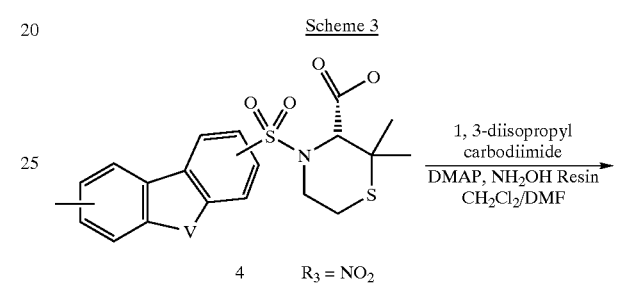

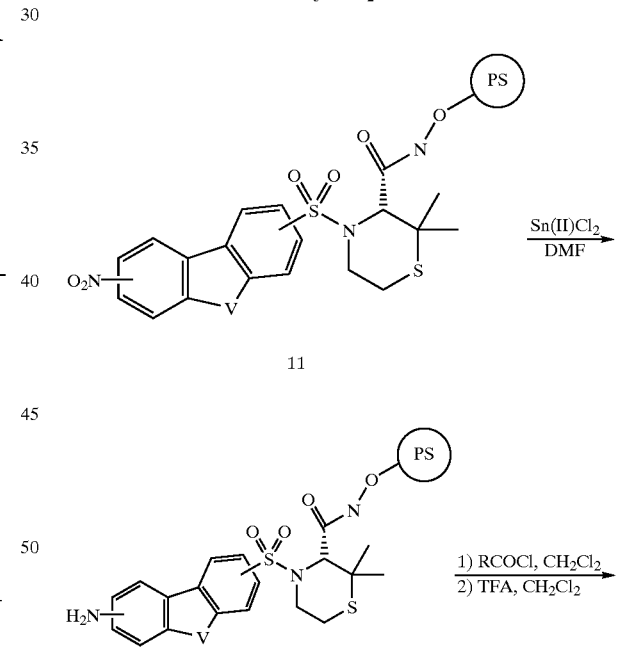

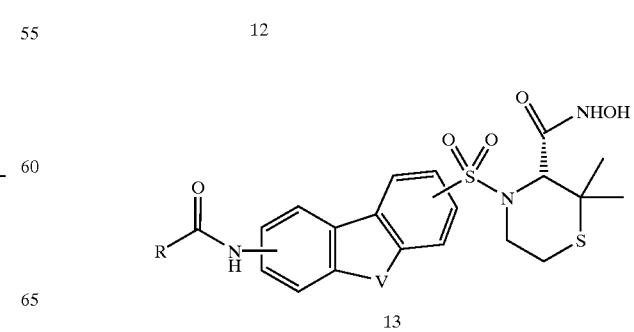

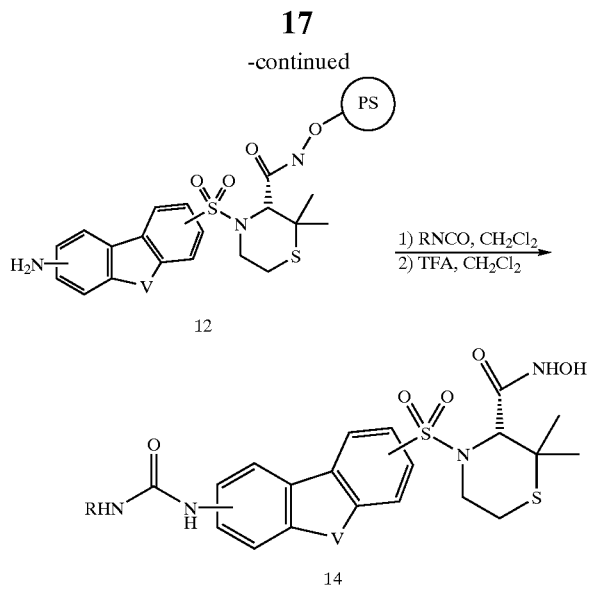

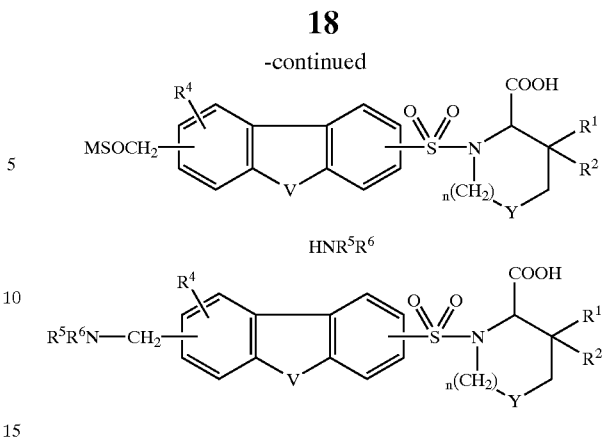

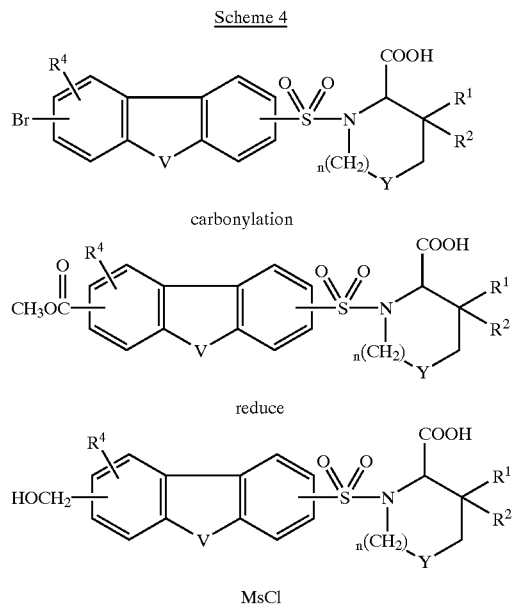

Scheme 4 illustrates the further modification of ring substituents or the tricyclic portion of the compounds of Formula I. The scheme starts with a halo (Br) substituted tricyclic analog that is carbomylated by reaction with carbon monoxide in the presence of a suitable catalyst to produce an alkoxycarbonyl substituted analog. The alkoxycarbonyl group is reduced to a hydroxymethyl group by reaction with a reducing agent such as sodium borohydride. The hydroxymethyl group is converted to a mesyloxymethyl group by reaction with methanesulfonyl chloride (MSCl). The mesyloxy group is readily displaced by reaction with a nucleophile such as an amine (HNR$^5$R$^6$) to afford various invention compounds of Formula I. As described above, the thiomorpholine carboxylic acids (X=OH) are readily converted to hydroxamic acids (X=NHOH) by reaction with hydroxylamine, or the entire foregoing sequence can be carried out on a hydroxylamine resin as described in Scheme 3.

During the synthesis of some of the invention compounds, it may be desirable to protect reactive functional groups such as hydroxy, amino, and carboxylic groups, so as to avoid unwanted side reactions. The use of protecting groups in synthetic organic chemistry is well-established and is fully described by Greene and Wuts in "Protecting Groups in Organic Synthesis" (John Wiley & Son Press, 3$^{rd}$ ed). Examples of common amino protecting groups include acyl groups such as formyl and acetyl, and arylalkyl groups such as benzyl. Typical hydroxy protecting groups include ether forming groups such as methyl and ethyl, and acyl groups such as acetyl and tert-butoxycarbonyl (tBOC). Carboxylic acids generally are protected as esters, for example 2,2,2-trichloroethyl and benzyl. These protecting groups are readily cleaved by standard methods when desired.

Sulfoxides and sulfones of Formula I, wherein n is 1 or 2, are prepared by oxidation of the corresponding sulfides with one or two equivalents of an oxidizing agent such as peracetic acid or meta-chloroperbenzoic acid.

The following detailed examples further illustrate the synthesis of typical invention compounds of Formula I. The examples are representative only and are not to be construed as limiting the invention in any respect. All references cited herein are incorporated by reference.

EXAMPLE 1

(S)-4-(Dibenzofuran-3-sulfonyl)-2,2-dimethyl-thiomorpholine-3-carboxylic Acid (a) To a solution of 3-dibenzofuransulfonyl chloride (1 g, 3.75 mmol) and 3(S)-2,2-dimethyl-3-thiomorpholine carboxylic acid, 1,1-dimethylether ester hydrochloride (1 g, 3.75 mmol) in 40 mL of dichloromethane was added triethylamine (1 mL). The solution was stirred at room temperature overnight, then added to 50 mL of water. The organic layer was separated, washed with brine, dried (MgSO4), filtered, and the solvent was removed by evaporation under reduced pressure. The crude product was recrystallized from hexane/ethyl acetate to give 0.68 g of (S)-4-(dibenzofuran-3-sulfonyl)-2,2-dimethyl-thiomorpholine-3-carboxylic acid tert-butyl ester. $^1$HNMR (DMSO-d$_6$) δ8.4 (d, 1H), 8.3 (d, 1H), 8.0 (s, 1H), 7.8 (m, 2H), 7.6 (t, 1H), 4.3 (s, 1H), 4.1 (dd, 1H), 3.7 (tt, 1H), 2.9 (tt, 1H), 2.6 (dd, 1H), 1.5 (s, 3H), 1.3 (s, 3H), 1.1 (s, 9H) ppm.

(b) The ester obtained in (a) (0.5 g, 1.08 mmol) was dissolved in dichloromethane (5 mL) to which was added one equivalent of anisole (0.1 mL, 1.08 mmol) and trifluoroacetic acid (5 mL). The solution was stirred at room temperature overnight and concentrated in vacuo. The crude product was recrystallized from hexane/ethyl acetate to give 0.42 g of the title compound. $^1$HNMR (DMSO-d$_6$) δ8.4 (d, 1H), 8.3 (d, 1H), 8.0 (s, 1H), 7.8 (m, 1H), 7.6 (t, 1H), 7.5 (t, 1H), 4.3 (s, 1H), 4.1 (d, 1H), 3.7 (tt, 1H), 3.0 (tt, 1H), 2.5 (d, 1H), 1.5 (s, 3H), 1.3 (s, 3H) ppm.

EXAMPLE 2
(S)-4-(Dibenzofuran-3-sulfonyl)-2,2-dimethyl-thiomorpholine-3-carboxylic Acid Hydroxyamide A dichloromethane solution of the acid synthesized in Example 1 (0.26 g, 0.64 mmol/10 mL CH2Cl2) was reacted with oxalyl chloride (0.1 mL, 0.77 mmol) and a catalytic amount of N,N-dimethylformamide under an atmosphere of nitrogen. After stirring at room temperature for 30 minutes, the solution was concentrated in vacuo. The crude acid chloride was dissolved in tetrahydrofuran and added to a tetrahydrofuran (60 mL)/water (20 mL) solution containing hydroxylamine hydrochloride (0.44 g, 6.4 mmol) and sodium bicarbonate (0.81 g, 9.6 mmol). The reaction mixture was stirred at room temperature overnight, then concentrated in vacuo. The crude product was diluted with ethyl acetate and washed with water, brine, dried (MgSO$_4$), and concentrated. The resulting residue was recrystallized from hexane/ethyl acetate to give 0.14 g of the title compound.

EXAMPLES 3–4

Replacement of 3(S)-2,2-dimethyl-3-thiomorpholine carboxylic acid, 1,1-dimethylethyl ester hydrochloride with R-5,5-dimethyl-thiazolidine-4-carboxylic acid tert-butyl ester and following the experimental conditions described for Examples 1 and 2 yield the following compounds:

EXAMPLE 3
R-3-(Dibenzofuran-3-sulfonyl)-5,5-dimethyl-thiazolidine-4-carboxylic Acid.

$^1$HNMR (DMSO-d$_6$) δ8.4 (d, 1H), 8.3 (d, 1H), 8.2 (s, 1H), 7.9 (d, 1H), 7.8 (d, 1H), 7.7 (t, 1H), 7.5 (t, 1H), 4.7 (dd, 2H), 4.1 (s, 1H), 1.3 (s, 3H), 1.2 (s, 3H) ppm.

EXAMPLE 4
R-3-(Dibenzofuran-3-sulfonyl)-5,5-dimethyl-thiazolidine-4-carboxylic Acid Hydroxyamide.

$^1$HNMR (DMSO-d$_6$) δ10.8 (s, 1H), 9.1 (s, 1H), 8.4 (d, 1H), 8.3 (d, 1H), 8.1 (s, 1H), 7.9 (d, 1H), 7.8 (d, 1H), 7.6 (t, 1H), 7.5 (t, 1H), 4.7 (s, 2H), 3.8 (s, 1H), 1.3 (s, 3H), 1.0 (s, 3H) ppm.

EXAMPLES 5–6

Replacement of 3-dibenzofuransulfonyl chloride with 2-fluorenesulfonyl chloride and utilizing the experimental conditions described in Example 1 and Example 2 gave the following compounds:

EXAMPLE 5
(S)-4-(9H-Fluorene-2-sulfonyl)-2,2-dimethyl-thiomorpholine-3-carboxylic Acid.

$^1$HNMR (DMSO-d$_6$) δ12.8 (bs, 1H), 8.1 (d, 1H), 8.0 (d, 1H), 7.9 (s, 1H), 7.7 (d, 1H), 7.6 (d, 1H), 7.4 (m, 2H), 4.3 (s, 1H), 4.0 (d, 1H), 3.7 (tt, 1H), 2.9 (tt, 1H), 2.5 (d, 1H), 1.5 (s, 3H), 1.3 (s, 3H) ppm.

EXAMPLE 6
(S)-4-(9H-Fluorene-2-sulfonyl)-2,2-dimethyl-thiomorpholine-3-carboxylic Acid Hydroxyamide.

EXAMPLES 7–8

Replacement of 3-dibenzofuransulfonyl chloride with 2-dibenzofuransulfonyl chloride and utilizing the experimental conditions described in Examples 1 and 2 gave the following compounds:

EXAMPLE 7
(S)-4-(Dibenzofuran-2-sulfonyl)-2,2-dimethyl-thiomorpholine-3-carboxylic Acid.

$^1$HNMR (DMSO-d$_6$) δ8.6 (s, 1H), 8.3 (d, 1H), 7.8 (m, 2H), 7.7 (d, 1H), 7.6 (t, 1H), 7.5 (t, 1H), 4.3 (s, 1H), 4.1 (d, 1H), 3.7 (t, 1H), 2.9 (t, 1H), 2.5 (d, 1H), 1.5 (s, 3H), 1.3 (s, 3H) ppm.

EXAMPLE 8
(S)-4-(Dibenzofuran-2-sulfonyl)-2,2-dimethyl-thiomorpholine-3-carboxylic Acid Hydroxyamide.

$^1$HNMR (DMSO-d$_6$) δ10.7 (s, 1H), 8.8 (s, 1H), 8.6 (s, 1H), 8.3 (d, 1H), 7.9 (m, 2H), 7.8 (d, 1H), 7.6 (t, 1H), 7.5 (t, 1H), 4.1 (s, IH), 4.0–3.9 (m, 2H), 2.9 (tt, 1H), 2.5 (d, 1H), 1.4 (s, 3H), 1.1 (s, 3H) ppm.

EXAMPLES 9–14

Replacement of 2-dibenzofuransulfonyl chloride in Example 7 with appropriately substituted dibenzofuran derivatives yield the following analogs:

EXAMPLE 9
9.(S)-4-(7-Bromo-dibenzofuran-2-sulfonyl)-2,2-dimethyl-thiomorpholine-3-carboxylic Acid.

$^1$HNMR (DMSO d$_6$) δ12.7 (s, 1H), 8.7 (s, 1H), 8.3 (d, 1H), 8.1 (s, 1H), 7.9 (m, 2H), 7.7 (d, 1H), 4.3 (s, 1H), 4.0 (d, 1H), 2.9 (t, 1H), 2.5 (d, 1H), 1.4 (s, 3H), 1.2 (s, 3H) ppm.

EXAMPLE 10
(S)-4-(7-Bromo-dibenzofuran-2-sulfonyl)-2,2-dimethyl-thiomorpholine-3-carboxylic Acid Hydroxyamide.

$^1$HNMR (DMSO-d$_6$) δ10.7 (s, 1H), 8.9 (s, 1H), 8.6 (s, 1H), 8.2 (d, 1H), 8.1 (s, 1H), 7.9 (m, 2H), 7.7 (d, 1H), 4.1 (s, 1H), 4.0–3.8 (m, 2H), 2.9 (t, 1H), 2.6 (d, 1H), 1.4 (s, 3H), 1.1 (s, 3H) ppm.

EXAMPLE 11
(S)-4-(7-Methoxycarbonyl-dibenzofuran-2-sulfonyl)-2,2-dimethyl-thiomorpholine-3-carboxylic Acid.

$^1$HNMR (DMSO-d$_6$) δ12.7 (s, 1H), 8.7 (s, 1H), 8.5 (d, 1H), 8.3 (s, 1H), 8.1 (d, 1H), 7.9 (m, 2H), 4.3 (s, 1H), 4.1 (d, 1H), 3.9 (s, 3H), 3.7 (t, 1H), 2.9 (t, 1H), 2.6 (d, 1H), 1.4 (s, 3H), 1.2 (s, 3H) ppm.

EXAMPLE 12
(S)-4-(7-Methoxycarbonyl-dibenzofuran-2-sulfonyl)-2,2-dimethyl-thiomorpholine-3-carboxylic Acid Hydroxyamide.

$^1$HNMR (DMSO-d$_6$) δ10.7 (s, 1H), 8.8 (s, 1H), 8.7 (s, 1H), 8.4 (d, 1H), 8.3 (s, 1H), 8.1 (d, 1H), 7.9 (m, 2H), 4.1 (s, 1H), 4.0 (m, 2H), 3.9 (s, 3H), 2.9 (t, 1H), 2.6 (d, 1H), 1.4 (s, 3H), 1.2 (s, 3H) ppm.

EXAMPLE 13
(S)-2,2-Dimethyl-4-(7-nitro-dibenzofuran-2-sulfonyl)-thiomorpholine-3-carboxylic Acid.

$^1$HNMR (DMSO-d$_6$) δ8.4 (d, 2H), 8.3 (d, 1H), 8.1 (d, 1H), 7.9 (d, 1H), 7.7 (d, 1H), 4.4 (s, 1H), 4.0 (d, 1H), 3.8 (t, 1H), 3.1 (t, 1H), 2.4 (d, 1H), 1.6 (s, 3H), 1.3 (s, 3H) ppm.

EXAMPLE 14
(S)-2,2-Dimethyl-4-(7-nitro-dibenzofuran-2-sulfonyl)-thiomorpholine-3-carboxylic Acid Hydroxyamide.

$^1$HNMR (DMSO-d$_6$) δ10.7 (s, 1H), 8.8 (s, 1H), 8.7 (s, 1H), 8.5 (d, 1H), 8.4 (d, 1H), 7.9 (m, 2H), 4.1 (s. 1H), 4.0 (m, 2H), 2.9 (t, 1H), 2.5 (d, 1H), 1.4 (s, 3H), 1.2 (s, 3H) ppm.

EXAMPLE 15

(S)-4-(Dibenzofuran-2-sulfonyl)-2,2-dimethyl-1,1-dioxo-thiomorpholine-3-carboxylic Acid Hydroxyamide To a chloroform solution of the compound prepared in Example 8 (0.052 g, 0.124 mmol/5 mL $CHCl_3$) stirred at room temperature under nitrogen was added dropwise peracetic acid. Dissolution occurred followed by precipitation. The reaction mixture was stirred at room temperature overnight, then concentrated in vacuo. The resulting residue was recrystallized from hexane/ethyl acetate to give 0.32 g of the titled sulfone. $^1$H R (DMSO-$d_6$) δ10.6 (s, 1H), 9.0 (bs, 1H), 8.6 (s, 1H), 8.3 (d, 1H), 8.9–8.7 (m, 3H), 7.6 (t, 1H), 7.5 (t, 1H), 4.7 (t, 1H), 5.5 (s, 1H), 3.5–3.2 (m, 2H), 1.4 (s, 3H), 1.3 (s, 3H) ppm.

EXAMPLES 16–24

General Procedure Utilizing Solid Phase Synthesis to Obtain Carboxylic Acid Derivatives (Scheme 2)

(a) To a suspension of Wang resin (2 g, 2.8 mmol) in 20 mL of dimethylformamide was added the acid 4 (2.2 g, 5.6 mmol) dissolved in 5 mL of dimethylformamide followed by the addition of pyridine (560 µL, 8.4 mmol) and 2,6-dichlorobenzoyl chloride (650 µL, 5.6 mmol). After the mixture was shaken for 22 hours at room temperature, the modified resin was filtered, washed 4×20 mL with dimethylformamide and 4×20 mL with dichloromethane, and dried under vacuum overnight to give resin 7.

(b) To 100 mg of modified resin 7 (0.93 mmol) was added 2 mL of 1 M tin (II) chloride dihydrate in dimethylformamide. After the reaction mixture was shaken for 16 hours at 50° C., the resin was filtered, washed 4×2 mL with dimethylformamide and 4×2 mL with dichloromethane, and dried under vacuum overnight to give resin 8.

(c) To the resin 8 was added 2 mL of 0.2 M acid chloride in dichloromethane and 0.5 mL of 0.4 M triethylamine in dichloromethane. After shaking for 16 hours at room temperature, the resin mixture was filtered, washed 3×2 nL with dichloromethane, 3×2 mL with methanol, 3×2 mL with dimethylformamide, 3×2 mL with dichloromethane, and dried under vacuum overnight. The final product 9 was obtained by the addition of 2 mL of 50% trifluoroacetic acid in dichloromethane. After 1 hour of shaking, the filtrate was collected and the solvent was removed under vacuum to give crude 9. The products are purified using silica gel chromatography and characterized by LC-MS.

EXAMPLE 16

(S)-4-(7-Isobutyrylamino-dibenzofuran-2-sulfonyl)-2,2-dimethyl-thiomorpholine-3-carboxylic Acid

EXAMPLE 17

(S)-2,2-Dimethyl-4-[7-(3-phenyl-propionylamino)-dibenzofuran-2-sulfonyl]-thiomorpholine-3-carboxylic Acid

EXAMPLE 18

(S)-2,2-Dimethyl-4-[7-(4-methyl-pentanoylamino)-dibenzofuran-2-sulfonyl]-thiomorpholine-3-carboxylic Acid

EXAMPLE 19

(S)-4-(7-Benzoylamino-dibenzofuran-2-sulfonyl)-2,2-dimethyl-thiomorpholine-3-carboxylic Acid

EXAMPLE 20

(S)-2,2-Dimethyl-4-(7-propionylamino-dibenzofuran-2-sulfonyl)-thiomorpholine-3-carboxylic Acid General Procedure for Urea Formation (Scheme 2).

To the resin 8 was added 2 mL of 0.2 M isocyanate in dioxane. After shaking for 16 hours at 80° C., the resin mixture was filtered, washed 4×2 mL with dimethylformamide and 4×2 mL with dichloromethane, and dried under vacuum overnight. A solution of $CH_2Cl_2$/TFA (50%) was then added to the dried resin. The mixture was stirred for 3 hours at room temperature. The resin was removed by filtration and washed twice with $CH_2Cl_2$ (1 mL). The washings were combined with the filtrate and concentrated in vacuo. Purification by silica gel chromatography followed by characterization by LC/MS yield the title compounds.

EXAMPLE 21

(S)-4-[7-(3-Ethyl-ureido)-dibenzofuran-2-sulfonyl]-2,2-dimethyl-thiomorpholine-3-carboxylic Acid

EXAMPLE 22

(S)-4-[7-(3-Isopropyl-ureido)-dibenzofuran-2-sulfonyl]-2,2-dimethyl-thiomorpholine-3-carboxylic Acid

EXAMPLE 23

(S)-2,2-Dimethyl-4-[7-(3-phenyl-ureido)-dibenzofuran-2-sulfonyl]-2,2-dimethyl-thiomorpholine-3-carboxylic Acid

EXAMPLE 24

(S)-4-[7-(3,3-Diethyl-ureido)-dibenzofuran-2-sulfonyl]-2,2-dimethyl-thiomorpholine-3-carboxylic Acid

EXAMPLES 25–33

General Procedure for Solid Phase Synthesis of Hydroxyamide Derivatives (Scheme 3).

a) To a suspension of hydroxylamine resin (1.5 g, 2.24 mmol) in DMF/$CH_2Cl_2$ (20 mL, 1:1) was added carboxylic acid 4 (2.6 g, 6.7 mmol) dissolved in DMF (5 mL). 1,3-Diisopropylcarbodiimide (1 mL, 6.7 mmol) and 4-(dimethylamino)pyridine (0.024 g, 0.2 mmol) were added, and the resulting mixture was shaken for 22 hours at room temperature. The resin was filtered, washed 4 times with DMF (20 mL each) and 4 times with $CH_2Cl_2$ (20 mL), then dried in vacuo overnight to give resin 11.

Utilizing steps (b) and (c) of Example 16 on the resin synthesized in (a) yield compounds of formula 13.

EXAMPLE 25

(S)-4-[7-(2,4-Dichloro-benzoylamino)-dibenzofuran-2-sulfonyl]-2,2-dimethyl-thiomorpholine-3-carbxoylic Acid Hydroxyamide

EXAMPLE 26

(S)-4-[7-(3,4-Dimethoxy-benzoylamino)-dibenzofuran-2-sulfonyl]-2,2-dimethyl-thiomorpholine-3-carboxylic Acid Hydroxyamide

EXAMPLE 27

(S)-4-[7-(2,5-Dimethoxy-benzoylamino)-dibenzofuran-2-sulfonyl]-2,2-dimethyl-thiomorpholine-3-carboxylic Acid Hydroxyamide

EXAMPLE 28

(S)-2,2-Dimethyl-4-(7-phenylacetylamino-dibenzofuran-2-sulfonyl)-thiomorpholine-3-carboxylic Acid Hydroxyamide

EXAMPLE 29

(S)-2,2-Dimethyl-4-{7-[(thiophene-2-carbonyl)-amino]-dibenzofuran-2-sulfonyl}-thiomorpholine-3-carboxylic Acid Hydroxyamide Replacement of acid chloride in Example 25 with appropriately substituted isocyanates yield the following urea derivatives:

EXAMPLE 30

(S)-4-[7-(3-Ethyl-ureido)-dibenzofuran-2-sulfonyl]-2,2-dimethyl-thiomorpholine-3-carboxylic Acid Hydroxyamide

EXAMPLE 31
(S)-4-[7-(3-Isopropyl-ureido)-dibenzofuran-2-sulfonyl]-2,2-dimethyl-thiomorpholine-3-carboxylic Acid Hydroxyamide

EXAMPLE 32
(S)-2,2-Dimethyl-4-[7-(3-phenyl-ureido)-dibenzofuran-2-sulfonyl]-2,2-dimethyl-thiomorpholine-3-carboxylic Acid Hydroxyamide

EXAMPLE 33
(S)-4-[7-(3,3-Diethyl-ureido)-dibenzofuran-2-sulfonyl]-2,2-dimethyl-thiomorpholine-3-carboxylic Acid Hydroxyamide By following the general procedures described above, the following invention compounds are similarly prepared:

2,2-Dimethyl-4-[7-(3-nitro-benzoylamino)-dibenzofuran-2-sulfonyl]-thiomorpholine-3-carboxylic acid hydroxyamide;

4-(7-Dodecanoylamino-dibenzofuran-2-sulfonyl)-2,2-dimethyl-thiomorpholine-3-carboxylic acid hydroxyamide;

N-[8-(3-Hydroxycarbamoyl-2,2-dimethyl-thiomorpholine-4-sulfonyl)-dibenzofuran-3-yl]-oxalamic acid ethyl ester;

4-[7-(Cyclohexanecarbonyl-amino)-dibenzofuran-2-sulfonyl]-2,2-dimethyl-thiomorpholine-3-carboxylic acid hydroxyamide;

4-[7-(2-Fluoro-benzoylamino)-dibenzofuran-2-sulfonyl]-2,2-dimethyl-thiomorpholine-3-carboxylic acid hydroxyamide;

4-(7-Acetylamino-dibenzofuran-2-sulfonyl)-2,2-dimethyl-thiomorpholine-3-carboxylic acid hydroxyamide;

Acetic acid 2-[8-(3-hydroxycarbamoyl-2,2-dimethyl-thiomorpholine-4-sulfonyl)-dibenzofuran-3-ylcarbamoyl]-phenyl ester;

4-(7-Benzoylamino-dibenzofuran-2-sulfonyl)-2,2-dimethyl-thiomorpholine-3-carboxylic acid hydroxyamide;

4-(7-Butyrylamino-dibenzofuran-2-sulfonyl)-2,2-dimethyl-thiomorpholine-3-carboxylic acid hydroxyamide;

4-(7-Decanoylamino-dibenzofuran-2-sulfonyl)-2,2-dimethyl-thiomorpholine-3-carboxylic acid hydroxyamide;

4-(7-Decanoylamino-dibenzofuran-2-sulfonyl)-2,2-dimethyl-thiomorpholine-3-carboxylic acid hydroxyamide;

4-(7-Diphenylacetylamino-dibenzofuran-2-sulfonyl)-2,2-dimethyl-thiomorpholine-3-carboxylic acid hydroxyamide;

4-{7-[2-(4-Chloro-phenoxy)-acetylamino]-dibenzofuran-2-sulfonyl}-2,2-dimethyl-thiomorpholine-3-carboxylic acid hydroxyamide;

N-[8-(3-Hydroxycarbamoyl-2,2-dimethyl-thiomorpholine-4-sulfonyl)-dibenzofuran-3-yl]-succinamic acid methyl ester;

4-[7-(3,4-Dimethoxy-benzoylamino)-dibenzofuran-2-sulfonyl]-2,2-dimethyl-thiomorpholine-3-carboxylic acid hydroxyamide;

4-[7-(2-Methoxy-benzoylamino)-dibenzofuran-2-sulfonyl]-2,2-dimethyl-thiomorpholine-3-carboxylic acid hydroxyamide;

4-[7-(2,2-Dimethyl-pentanoylamino)-dibenzofuran-2-sulfonyl]-2,2-dimethyl-thiomorpholine-3-carboxylic acid hydroxyamide;

4-[7-(2,4-Dichloro-benzoylamino)-dibenzofuran-2-sulfonyl]-2,2-dimethyl-thiomorpholine-3-carboxylic acid hydroxyamide;

4-[7-(2,5-Dimethoxy-benzoylamino)-dibenzofuran-2-sulfonyl]-2,2-dimethyl-thiomorpholine-3-carboxylic acid hydroxyamide;

2,2-Dimethyl-4-[7-(4-methyl-pentanoylamino)-dibenzofuran-2-sulfonyl]-thiomorpholine-3-carboxylic acid hydroxyamide;

4-[7-(Cyclopropanecarbonyl-amino)-dibenzofuran-2-sulfonyl]-2,2-dimethyl-thiomorpholine-3-carboxylic acid hydroxyamide;

Acetic acid [8-(3-hydroxycarbamoyl-2,2-dimethyl-thiomorpholine-4-sulfonyl)-dibenzofuran-3-ylcarbamoyl]-phenyl-methyl ester;

2,2-Dimethyl-4-{7-[(tricyclo[3.3.1]decanane-1-carbonyl)-amino]-dibenzofuran-2-sulfonyl}-thiomorpholine-3-carboxylic acid hydroxyamide;

2,2-Dimethyl-4-(7-pentanoylamino-dibenzofuran-2-sulfonyl)-thiomorpholine-3-carboxylic acid hydroxyamide;

4-[7-(2,2-Dimethyl-propionylamino)-dibenzofuran-2-sulfonyl]-2,2-dimethyl-thiomorpholine-3-carboxylic acid hydroxyamide;

2,2-Dimethyl-4-[7-((Z)-octadec-9-enoylamino)-dibenzofuran-2-sulfonyl]-thiomorpholine-3-carboxylic acid hydroxyamide;

N-[8-(3-Hydroxycarbamoyl-2,2-dimethyl-thiomorpholine-4-sulfonyl)-dibenzofuran-3-yl]-succinamic acid ethyl ester;

4-(7-Isobutyrylamino-dibenzofuran-2-sulfonyl)-2,2-dimethyl-thiomorpholine-3-carboxylic acid hydroxyamide;

4-(7-Isobutyrylamino-dibenzofuran-2-sulfonyl)-2,2-dimethyl-thiomorpholine-3-carboxylic acid hydroxyamide;

4-[7-(3-Chloro-benzoylamino)-dibenzofuran-2-sulfonyl]-2,2-dimethyl-thiomorpholine-3-carboxylic acid hydroxyamide;

2,2-Dimethyl-4-(7-nonanoylamino-dibenzofuran-2-sulfonyl)-thiomorpholine-3-carboxylic acid hydroxyamide;

2,2-Dimethyl-4-[7-(2-trifluoromethyl-benzoylamino)-dibenzofuran-2-sulfonyl]-thiomorpholine-3-carboxylic acid hydroxyamide;

2,2-Dimethyl-4-[7-(2-trifluoromethyl-benzoylamino)-dibenzofuran-2-sulfonyl]-thiomorpholine-3-carboxylic acid hydroxyamide;

2,2-Dimethyl-4-(7-octanoylamino-dibenzofuran-2-sulfonyl)-thiomorpholine-3-carboxylic acid hydroxyamide;

4-(7-Hexadecanoylamino-dibenzofuran-2-sulfonyl)-2,2-dimethyl-thiomorpholine-3-carboxylic acid hydroxyamide;

4-(7-Hexadecanoylamino-dibenzofuran-2-sulfonyl)-2,2-dimethyl-thiomorpholine-3-carboxylic acid hydroxyamide;

2,2-Dimethyl-4-[7-(2,2,3,3,4,4,5,5,6,6,7,7,8,8,8-pentadecafluoro-octanoylamino)-dibenzofuran-2-sulfonyl]-thiomorpholine-3-carboxylic acid hydroxyamide;

2,2-Dimethyl-4-[7-(2-phenoxy-acetylamino)-dibenzofuran-2-sulfonyl]-thiomorpholine-3-carboxylic acid hydroxyamide;

2,2-Dimethyl-4-[7-(2-phenoxy-acetylamino)-dibenzofuran-2-sulfonyl]-thiomorpholine-3-carboxylic acid hydroxyamide;

2,2-Dimethyl-4-(7-phenylacetylamino-dibenzofuran-2-sulfonyl)-thiomorpholine-3-carboxylic acid hydroxyamide;

2,2-Dimethyl-4-(7-propionylamino-dibenzofuran-2-sulfonyl)-thiomorpholine-3-carboxylic acid hydroxyamide;

2,2-Dimethyl-4-(7-tridecanoylamino-dibenzofuran-2-sulfonyl)-thiomorpholine-3-carboxylic acid hydroxyamide;

4-[7-(3,5-Dinitro-benzoylamino)-dibenzofuran-2-sulfonyl]-2,2-dimethyl-thiomorpholine-3-carboxylic acid hydroxyamide;

N-[8-(3-Hydroxycarbamoyl-2,2-dimethyl-thiomorpholine-4-sulfonyl)-dibenzofuran-3-yl]-malonamic acid ethyl ester;

N-[8-(3-Hydroxycarbamoyl-2,2-dimethyl-thiomorpholine-4-sulfonyl)-dibenzofuran-3-yl]-malonamic acid ethyl ester;

2,2-Dimethyl-4-[7-(2,2,2-trichloro-acetylamino)-dibenzofuran-2-sulfonyl]-thiomorpholine-3-carboxylic acid hydroxyamide;

2,2-Dimethyl-4-{7-[(thiophene-2-carbonyl)-amino]-dibenzofuran-2-sulfonyl}-thiomorpholine-3-carboxylic acid hydroxyamide;

2,2-Dimethyl-4-[7-(3-phenyl-propionylamino)-dibenzofuran-2-sulfonyl]-thiomorpholine-3-carboxylic acid hydroxyamide; and 4-[7-(2-Bromo-benzoylamino)-dibenzofuran-2-sulfonyl]-2,2-dimethyl-thiomorpholine-3-carboxylic acid hydroxyamide.

The invention compounds of Formula I have been evaluated in standard assays for their ability to inhibit the catalytic activity of various MMP enzymes. The assays used to evaluate the biological activity of the invention compounds are well known and routinely used by those skilled in the study of MMP inhibitors and their use to treat clinical conditions.

The assays measure the amount by which a test compound reduces the hydrolysis of a thiopeptolide substrate catalyzed by a matrix metalloproteinase enzyme. Such assays are described in detail by Ye et al., *Biochemistry*, 1992;31(45):11231–11235, hereby incorporated herein by reference.

Thiopeptolide substrates show virtually no decomposition or hydrolysis at or below neutral pH in the absence of a matrix metalloproteinase enzyme. A typical thiopeptolide substrate commonly utilized for assays is Ac-Pro-Leu-Gly-thioester-Leu-Leu-Gly-OEt. A 100 μL assay mixture will contain 50 mM of N-2-hydroxyethylpiperazine-N'-2-ethanesulfonic acid buffer ("HEPES") at pH 7.0, 10 mM $CaCl_2$, 100 μM thiopeptolide substrate, and 1 mM 5,5'-dithio-bis-(2-nitrobenzoic acid) (DTNB). The thiopeptolide substrate concentration may be varied from, for example, 10 to 800 μM, in order to obtain Km and Kcat values. The change in absorbance at 405 nm is monitored on a Thermo Max microplate reader (Molecular Devices, Menlo Park, Calif.) at room temperature (22° C.). The calculation of the amount of hydrolysis of the thiopeptolide substrate is based on $E_{412}$=13600 $M^{-1}$ $cm^{-1}$ for the DTNB-derived product 3-carboxy-4-nitrothiophenoxide. Assays are carried out with and without matrix metalloproteinase inhibitor compounds, and the amount of hydrolysis is compared for a determination of inhibitory activity of the test compounds.

It should be appreciated that the assay buffer used with MMP-3CD is 50 mM of N-morpholinoethanesulfonate ("MES") at pH 6.0 rather than the HEPES buffer at pH 7.0 described above.

Several representative compounds have been evaluated for their ability to inhibit various matrix metalloproteinase enzymes. Table 1 below presents inhibitory activity for compounds from various classes. In Table 1, MMP-1FL refers to full-length interstitial collagenase; MMP-2FL refers to full-length Gelatinase A; MMP-3CD refers to the catalytic domain of stromelysin-1; MMP-7FL refers to full-length matrilysin; MMP-9FL refers to full-length Gelatinase B; MMP-13CD refers to the catalytic domain of collagenase 3; and MMP-14CD refers to the catalytic domain of MMP-14. Test compounds were evaluated at various concentrations, in order to determine their respective $IC_{50}$ values, the micromolar concentration of compound required to cause a 50% inhibition of the catalytic activity of the respective enzyme.

TABLE 1

| | ($IC_{50}$ in μM) | | | | | | |
|---|---|---|---|---|---|---|---|
| Example | MMP-1FL | MMP-2FL | MMP-3CD | MMP-7FL | MMP-9FL | MMP-13CD | MMP-14CD |
| 1 | 1.424 | 0.074 | 0.041 | 55 | 22.5 | 0.97 | 0.064 |
| 2 | 0.013 | 0.015 | 0.011 | 0.20 | 0.21 | 0.004 | 0.026 |
| 3 | 100 | 9.5 | 2.5 | 100 | 150 | 23 | 10 |
| 4 | 6.9 | 3.9 | 3.2 | 59 | 18 | 1.4 | 11 |
| 5 | 23 | 0.50 | 0.13 | 100 | 100 | 5.1 | 0.84 |
| 6 | 0.14 | 0.024 | 0.008 | 0.88 | 0.55 | 0.004 | 0.063 |
| 7 | 59 | 3.9 | 0.21 | 16 | 100 | 11 | 4 |
| 8 | 0.017 | 0.015 | 0.009 | 0.028 | 0.26 | 0.003 | 0.04 |
| 9 | 70 | 4 | 0.02 | 1.2 | 65 | 0.92 | 3.8 |
| 10 | 0.042 | 0.007 | 0.004 | 0.031 | 0.066 | 0.002 | 0.012 |
| 11 | 100 | 5.2 | 0.094 | 3.5 | 69 | 4.6 | 20 |
| 12 | 0.15 | 0.017 | 0.006 | 0.029 | 0.047 | 0.005 | 0.095 |
| 13 | 60 | 33 | 1 | 1.6 | 100 | 2.7 | 15 |
| 14 | 0.012 | 0.022 | 0.005 | 0.038 | 0.19 | 0.002 | 0.024 |
| 15 | .033 | .25 | .008 | .032 | 1.8 | .013 | .098 |

The foregoing data in Table 1 establish that the invention compounds of Formula I are potent inhibitors of MMP enzymes. Because of this potent inhibitory activity, the invention compounds are especially useful to treat diseases mediated by the MMP enzymes.

Administration of a compound of Formula I, or a pharmaceutically acceptable salt thereof, to a mammal to treat diseases mediated by MMP enzymes is preferably, although not necessarily, accomplished by administering the compound or the salt thereof, in a pharmaceutical dosage form.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I. The active compound generally is present in a concentration of about 5% to about 95% by weight of the formulation.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 to 1000 mg, preferably 10 to 100 mg according to the particular application and the potency of the active component. The composition can, if desired, also contain other compatible therapeutic agents.

In therapeutic use as agents to inhibit a matrix metalloproteinase enzyme for the treatment of atherosclerotic plaque rupture, aortic aneurism, heart failure, restenosis, periodontal disease, corneal ulceration, cancer metastasis, tumor angiogenesis, arthritis, or other autoimmune or inflammatory disorders dependent upon breakdown of connective tissue, the compounds utilized in the pharmaceutical method of this invention are administered at a dose that is effective to inhibit the hydrolytic activity of one or more matrix metalloproteinase enzymes. The initial dosage of about 1 mg/kg to about 100 mg/kg daily will be effective. A daily dose range of about 25 mg/kg to about 75 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired. Typical dosages will be from about 0.1 mg/kg to about 500 mg/kg, and ideally about 25 mg/kg to about 250 mg/kg, such that it will be an amount which is effective to treat the particular disease being prevented or controlled.

The following examples illustrate typical pharmaceutical compositions provided by the invention.

COMPOSITION EXAMPLE 1

| Tablet Formulation | |
| --- | --- |
| Ingredient | Amount (mg) |
| Compound of Example 1 | 25 |
| Lactose | 50 |
| Corn starch (for mix) | 10 |
| Corn starch (paste) | 10 |
| Magnesium stearate (1%) | 5 |
| Total | 100 |

The cyclic sulfonamide of Example 1, lactose, and corn starch (for mix) are blended to uniformity. The corn starch (for paste) is suspended in 200 mL of water and heated with stirring to form a paste. The paste is used to granulate the mixed powders. The wet granules are passed through a Number 8 hand screen and dried at 80° C. The dry granules are lubricated with the 1% magnesium stearate and pressed into a tablet. Such tablets can be administered to a human from one to four times a day for treatment of atherosclerosis and arthritis.

COMPOSITION EXAMPLE 2

| Preparation for Oral Solution | |
| --- | --- |
| Ingredient | Amount |
| Sorbitol solution (70% N.F.) | 40 mL |
| Compound of Example 3 | 400 mg |
| Sodium benzoate | 20 mg |
| Saccharin | 5 mg |
| Red dye | 10 mg |
| Cherry flavor | 20 mg |
| Distilled water q.s. | 100 mL |

The sorbitol solution is added to 40 mL of distilled water, and the cyclic sulfonamide of Example 3 is dissolved therein. The saccharin, sodium benzoate, flavor, and dye are added and dissolved. The volume is adjusted to 100 mL with distilled water. Each milliliter of syrup contains 4 mg of invention compound.

COMPOSITION EXAMPLE 3

Parenteral Solution

In a solution of 700 mL of propylene glycol and 200 mL of water for injection is suspended 20 g of the compound of Example 2. After suspension is complete, the pH is adjusted to 6.5 with 1N sodium hydroxide, and the volume is made up to 1000 mL with water for injection. The formulation is sterilized, filled into 5.0-mL ampoules each containing 2.0 mL, and sealed under nitrogen.

As matrix metalloproteinase inhibitors, the compounds of Formula I are useful as agents for the treatment of multiple sclerosis. They are also useful as agents for the treatment of atherosclerotic plaque rupture, restenosis, periodontal disease, corneal ulceration, treatment of burns, decubital ulcers, wound repair, heart failure, cancer metastasis, tumor angiogenesis, arthritis, and other inflammatory disorders dependent upon tissue invasion by leukocytes. The compounds are especially useful to treat rheumatoid arthritis and osteoarthritis.

It should be appreciated that in all invention embodiments described above or in the claims below, whenever an R group such as, for example, $R^1$, $R^2$, $R^3$, $R^4$, $R^5$, or $R^6$, is used more than once to define an invention compound, each use of the R group is independent of any other use of that same R group or, for that matter, any other R group, unless otherwise specified.

What is claimed is:

1. A compound of Formula I

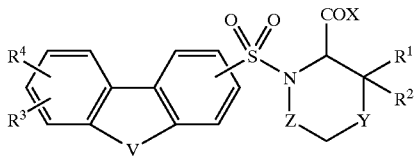

or a pharmaceutically acceptable salt thereof wherein:

$R^1$ and $R^2$ independently are hydrogen or $C_1$–$C_6$ alkyl;

$R^3$ and $R^4$ independently are hydrogen, halo, nitro, $NR^5R^6$, $C_1$–$C_6$ alkyl, $C_2$–$C_6$ alkenyl, $C_2$–$C_6$ alkynyl; $(CH_2)_mOH$, $(CH_2)_mOR^5$, $(CH_2)_m$ cycloalkyl, $(CH_2)_m$ aryl, $(CH_2)_m$ substituted aryl, $(CH_2)_m$ heteroaryl, $(CH_2)_m$ substituted heteroaryl, $(CH_2)_m$ carbocycle, $(CH_2)_m$ heterocycle; $(CH_2)_m NR^5R^6$, $NHCONR^5R^6$, $(CH_2)_mCOR^5$, $(CH_2)_mCONR^5R^6$, or $(CH_2)_mCO_2R^5$;

m is an integer from 0 to 6;

$R^5$ and $R^6$ independently are hydrogen or $C_1$–$C_6$ alkyl, or taken together with the nitrogen to which they are attached complete a 3- to 7-membered ring;

Z is $(CH_2)_n$;

n is 0, 1, or 2;

Y is S, SO, or $SO_2$;

X is OH or NHOH;

V is O, S, $SO_2$, NH, $NR^5$, or $CH_2$.

2. A compound of Formula II

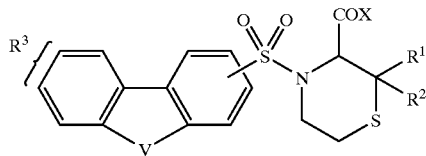

or a pharmaceutically acceptable salt thereof wherein:

$R^1$ and $R^2$ independently are hydrogen or $C_1$–$C_6$ alkyl;

$R^3$ is hydrogen, halo, nitro, $NR^5R^6$, $C_1$–$C_6$ alkyl, $C_2$–$C_6$ alkenyl, $C_2$–$C_6$ alkynyl; $(CH_2)_mOH$, $(CH_2)_mOR^5$, $(CH_2)_m$ cycloalkyl, $(CH_2)_m$ aryl, $(CH_2)_m$ substituted aryl, $(CH_2)_m$ heteroaryl, $(CH_2)_m$ substituted heteroaryl, $(CH_2)_m$ carbocycle, $(CH_2)_m$ heterocycle; $(CH_2)_m NR^5R^6$, $NHCONR^5R^6$, $(CH_2)_mCOR^5$, $(CH2)_m CONR^5R^6$, or $(CH_2)_mCO_2R^5$;

V is O, S, $SO_2$, NH, $NR^5$, or $CH_2$; and

X is OH or NHOH.

3. A compound of claim 2 wherein $R^1$ and $R^2$ are methyl.

4. A compound of claim 2 wherein X is OH.

5. A compound of claim 2 wherein X is NHOH.

6. A compound of Formula III

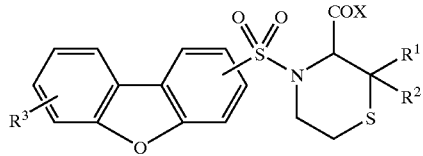

or a pharmaceutically acceptable salt thereof wherein:

$R^1$ and $R^2$ independently are hydrogen or $C_1$–$C_6$ alkyl;

$R^3$ is hydrogen, halo, nitro, $NR^5R^6$, $C_1$–$C_6$ alkyl, $C_2$–$C_6$ alkenyl, $C_2$–$C_6$ alkynyl; $(CH_2)_mOH$, $(CH_2)_mOR^5$, $(CH_2)_m$ cycloalkyl, $(CH_2)_m$ aryl, $(CH_2)_m$ substituted aryl, $(CH_2)_m$ heteroaryl, $(CH_2)_m$ substituted heteroaryl, $(CH_2)_m$ carbocycle, $(CH_2)_m$ heterocycle; $(CH_2)_m NR^5R^6$, $NHCONR^5R^6$, $(CH_2)_mCOR^5$, $(CH_2)_m CONR^5R^6$, or $(CH_2)_mCO_2R^5$; and X is OH or NHOH.

7. A compound of Formula IV

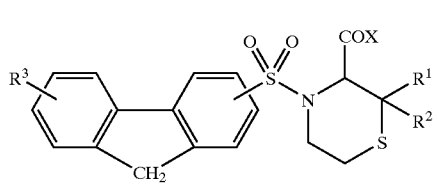

or a pharmaceutically acceptable salt thereof wherein:

$R^1$ and $R^2$ independently are hydrogen or $C_1$–$C_6$ alkyl;

$R^3$ is hydrogen, halo, nitro, $NR^5R^6$, $C_1$–$C_6$ alkyl, $C_2$–$C_6$ alkenyl, $C_2$–$C_6$ alkynyl; $(CH_2)_mOH$, $(CH_2)_mOR^5$, $(CH_2)_m$ cycloalkyl, $(CH_2)_m$ aryl, $(CH_2)_m$ substituted aryl, $(CH_2)_m$ heteroaryl, $(CH_2)_m$ substituted heteroaryl, $(CH_2)_m$ carbocycle, $(CH_2)_m$ heterocycle; $(CH_2)_m NR^5R^6$, $NHCONR^5R^6$, $(CH_2)_mCOR^5$, $(CH_2)_m CONR^5R^6$, or $(CH_2)_mCO_2R^5$; and X is OH or NHOH.

8. A compound of Formula V

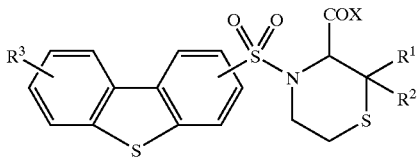

or a pharmaceutically acceptable salt thereof wherein:
$R^1$ and $R^2$ independently are hydrogen or $C_1$–$C_6$ alkyl;
$R^3$ is hydrogen, halo, nitro, $NR^5R^6$, $C_1$–$C_6$ alkyl, $C_2$–$C_6$ alkenyl, $C_2$–$C_6$ alkynyl; $(CH_2)_mOH$, $(CH_2)_mOR^5$, $(CH_2)_m$ cycloalkyl, $(CH_2)_m$ aryl, $(CH_2)_m$ substituted aryl, $(CH_2)_m$ heteroaryl, $(CH_2)_m$ substituted heteroaryl, $(CH_2)_m$ carbocycle, $(CH_2)_m$ heterocycle; $(CH_2)_m NR^5R^6$, $NHCONR^5R^6$, $(CH_2)_mCOR^5$, $(CH_2)_m CONR^5R^6$, or $(CH_2)_mCO_2R^5$; and
X is OH or NHOH.

9. A compound of Formula VI

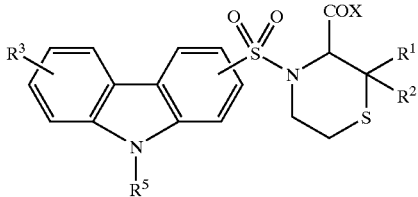

or a pharmaceutically acceptable salt thereof wherein:
$R^1$ and $R^2$ independently are hydrogen or $C_1$–$C_6$ alkyl;
$R^3$ is hydrogen, halo, nitro, $NR^5R^6$, $C_1$–$C_6$ alkyl, $C_2$–$C_6$ alkenyl, $C_2$–$C_6$ alkynyl; $(CH_2)_mOH$, $(CH_2)_mOR^5$, $(CH_2)_m$ cycloalkyl, $(CH_2)_m$ aryl, $(CH_2)_m$ substituted aryl, $(CH_2)_m$ heteroaryl, $(CH_2)_m$ substituted heteroaryl, $(CH_2)_m$ carbocycle, $(CH_2)_m$ heterocycle; $(CH_2)_m NR^5R^6$, $NHCONR^5R^6$, $(CH_2)_mCOR^5$, $(CH_2)_m CONR^5R^6$, or $(CH_2)_mCO_2R^5$; and
X is OH or NHOH.

10. A compound of Formula VII

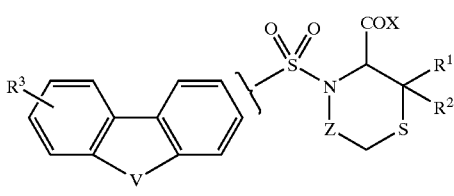

or a pharmaceutically acceptable salt thereof, wherein
$R^1$ and $R^2$ independently are hydrogen or $C_1$–$C_6$ alkyl;
$R^3$ is hydrogen, halo, nitro $NR^5R^5$, $C_1$–$C_6$ alkyl, $C_2$–$C_6$ alkenyl, $C_2$–$C_6$ alkynyl; $(CH_2)_mOH$, $(CH_2)_mOR_5$, $(CH_2)_m$ cycloalkyl, $(CH_2)_m$ aryl, $(CH_2)_m$ substituted aryl, $(CH_2)_m$ heteroaryl, $(CH_2)_m$ substituted heteroaryl, $(CH_2)_m$ carbocycle, $(CH_2)_m$ heterocycle; $(CH_2)_m NR^5R^6$, $(CH_2)_mCOR^5$, $(CH_2)_mCONR^5R^6$, or $(CH_2)_m CO_2R^5$;
m is an integer of from 0 to 6;
$R^5$ and $R^6$ independently are hydrogen or $C_1$–$C_6$ alkyl, or taken together with the nitrogen to which they are attached complete a 3- to 7-membered ring;
Z is $(CH_2)_n$;
n is 0, 1, or 2;
X is OH or NHOH;
V is O, S, $SO_2$, NH, $NR^5$, or $CH_2$.

11. A compound which is:
(S)-4-(Dibenzofuran-3-sulfonyl)-2,2-dimethyl-thiomorpholine-3-carboxylic acid;
(S)-4-(Dibenzofuran-3-sulfonyl)-2,2-dimethyl-thiomorpholine-3-carboxylic acid hydroxyamide;
R-3-(Dibenzofuran-3-sulfonyl)-5,5-dimethyl-thiazolidine-4-carboxylic acid;
R-3-(Dibenzofuran-3-sulfonyl)-5,5-dimethyl-thiazolidine-4-carboxylic acid hydroxyamide;
(S)-4-(9H-Fluorene-2-sulfonyl)-2,2-dimethyl-thiomorpholine-3-carboxylic acid;
(S)-4-(9H-Fluorene-2-sulfonyl)-2,2-dimethyl-thiomorpholine-3-carboxylic acid hydroxyamide;
(S)-4-(Dibenzofuran-2-sulfonyl)-2,2-dimethyl-thiomorpholine-3-carboxylic acid;
(S)-4-(Dibenzofuran-2-sulfonyl)-2,2-dimethyl-thiomorpholine-3-carboxylic acid hydroxyamide;
(S)-4-(7-Bromo-dibenzofuran-2-sulfonyl)-2,2-dimethyl-thiomorpholine-3-carboxylic acid;
(S)-4-(7-Bromo-dibenzofuran-2-sulfonyl)-2,2-dimethyl-thiomorpholine-3-carboxylic acid hydroxyamide;
(S)-4-(7-Methoxycarbonyl-dibenzofuran-2-sulfonyl)-2,2-dimethyl-thiomorpholine-3-carboxylic acid;
(S)-4-(7-Methoxycarbonyl-dibenzofuran-2-sulfonyl)-2,2-dimethyl-thiomorpholine-3-carboxylic acid hydroxyamide;
(S)-2,2-Dimethyl-4-(7-nitro-dibenzofuran-2-sulfonyl)-thiomorpholine-3-carboxylic acid;
(S)-2,2-Dimethyl-4-(7-nitro-dibenzofuran-2-sulfonyl)-thiomorpholine-3-carboxylic acid hydroxyamide;
(S)-4-(Dibenzofuran-2-sulfonyl)-2,2-dimethyl-1,1-dioxothiomorpholine-3-carboxylic acid hydroxyamide;
(S)-4-(7-Isobutyrylamino-dibenzofuran-2-sulfonyl)-2,2-dimethyl-thiomorpholine-3-carboxylic acid;
(S)-2,2-Dimethyl-4-[7-(3-phenyl-propionylamino)-dibenzofuran-2-sulfonyl]-thiomorpholine-3-carboxylic acid;
(S)-2,2-Dimethyl-4-[7-(4-methyl-pentanoylamino)-dibenzofuran-2-sulfonyl]-thiomorpholine-3-carboxylic acid;
(S)-4-(7-Benzoylamino-dibenzofuran-2-sulfonyl)-2,2-dimethyl-thiomorpholine-3-carboxylic acid;
(S)-2,2-Dimethyl-4-(7-propionylamino-dibenzofuran-2-sulfonyl)-thiomorpholine-3-carboxylic acid;
(S)-4-[7-(3-Ethyl-ureido)-dibenzofuran-2-sulfonyl]-2,2-dimethyl-thiomorpholine-3-carboxylic acid;
(S)-4-[7-(3-Isopropyl-ureido)-dibenzofuran-2-sulfonyl]-2,2-dimethyl-thiomorpholine-3-carboxylic acid;
(S)-2,2-Dimethyl-4-[7-(3-phenyl-ureido)-dibenzofuran-2-sulfonyl]-2,2-dimethyl-thiomorpholine-3-carboxylic acid;
(S)-4-[7-(3,3-Diethyl-ureido)-dibenzofuran-2-sulfonyl]-2,2-dimethyl-thiomorpholine-3-carboxylic acid;
(S)-4-[7-(2,4-Dichloro-benzoylamino)-dibenzofuran-2-sulfonyl]-2,2-dimethyl-thiomorpholine-3-carbxoylic acid hydroxyamide;
(S)-4-[7-(3,4-Dimethoxy-benzoylamino)-dibenzofuran-2-sulfonyl]-2,2-dimethyl-thiomorpholine-3-carboxylic acid hydroxyamide;

(S)-4-[7-(2,5-Dimethoxy-benzoylamino)-dibenzofuran-2-sulfonyl]-2,2-dimethyl-thiomorpholine-3-carboxylic acid hydroxyamide;

(S)-2,2-Dimethyl-4-(7-phenylacetylamino-dibenzofuran-2-sulfonyl)-thiomorpholine-3-carboxylic acid hydroxyamide;

(S)-2,2-Dimethyl-4-{7-[(thiophene-2-carbonyl)-amino]-dibenzofuran-2-sulfonyl}-thiomorpholine-3-carboxylic acid hydroxyamide;

(S)-4-[7-(3-Ethyl-ureido)-dibenzofuran-2-sulfonyl]-2,2-dimethyl-thiomorpholine-3-carboxylic acid hydroxyamide;

(S)-4-[7-(3-Isopropyl-ureido)-dibenzofuran-2-sulfonyl]-2,2-dimethyl-thiomorpholine-3-carboxylic acid hydroxyamide;

(S)-2,2-Dimethyl-4-[7-(3-phenyl-ureido)-dibenzofuran-2-sulfonyl]-2,2-dimethyl-thiomorpholine-3-carboxylic acid hydroxyamide;

(S)-4-[7-(3,3-Diethyl-ureido)-dibenzofuran-2-sulfonyl]-2,2-dimethyl-thiomorpholine-3-carboxylic acid hydroxyamide;

2,2-Dimethyl-4-[7-(3-nitro-benzoylamino)-dibenzofuran-2-sulfonyl]-thiomorpholine-3-carboxylic acid hydroxyamide;

4-(7-Dodecanoylamino-dibenzofuran-2-sulfonyl)-2,2-dimethyl-thiomorpholine-3-carboxylic acid hydroxyamide;

N-[8-(3-Hydroxycarbamoyl-2,2-dimethyl-thiomorpholine-4-sulfonyl)-dibenzofuran-3-yl]-oxalamic acid ethyl ester;

4-[7-(Cyclohexanecarbonyl-amino)-dibenzofuran-2-sulfonyl]-2,2-dimethyl-thiomorpholine-3-carboxylic acid hydroxyamide;

4-[7-(2-Fluoro-benzoylamino)-dibenzofuran-2-sulfonyl]-2,2-dimethyl-thiomorpholine-3-carboxylic acid hydroxyamide;

4-(7-Acetylamino-dibenzofuran-2-sulfonyl)-2,2-dimethyl-thiomorpholine-3-carboxylic acid hydroxyamide;

Acetic acid 2-[8-(3-hydroxycarbamoyl-2,2-dimethyl-thiomorpholine-4-sulfonyl)-dibenzofuran-3-ylcarbamoyl]-phenyl ester;

4-(7-Benzoylamino-dibenzofuran-2-sulfonyl)-2,2-dimethyl-thiomorpholine-3-carboxylic acid hydroxyamide;

4-(7-Butyrylamino-dibenzofuran-2-sulfonyl)-2,2-dimethyl-thiomorpholine-3-carboxylic acid hydroxyamide;

4-(7-Decanoylamino-dibenzofuran-2-sulfonyl)-2,2-dimethyl-thiomorpholine-3-carboxylic acid hydroxyamide;

4-(7-Decanoylamino-dibenzofuran-2-sulfonyl)-2,2-dimethyl-thiomorpholine-3-carboxylic acid hydroxyamide;

4-(7-Diphenylacetylamino-dibenzofuran-2-sulfonyl)-2,2-dimethyl-thiomorpholine-3-carboxylic acid hydroxyamide;

4-{7-[2-(4-Chloro-phenoxy)-acetylamino]-dibenzofuran-2-sulfonyl}-2,2-dimethyl-thiomorpholine-3-carboxylic acid hydroxyamide;

N-[8-(3-Hydroxycarbamoyl-2,2-dimethyl-thiomorpholine-4-sulfonyl)-dibenzofuran-3-yl]-succinamic acid methyl ester;

4-[7-(3,4-Dimethoxy-benzoylamino)-dibenzofuran-2-sulfonyl]-2,2-dimethyl-thiomorpholine-3-carboxylic acid hydroxyamide;

4-[7-(2-Methoxy-benzoylamino)-dibenzofuran-2-sulfonyl]-2,2-dimethyl-thiomorpholine-3-carboxylic acid hydroxyamide;

4-[7-(2,2-Dimethyl-pentanoylamino)-dibenzofuran-2-sulfonyl]-2,2-dimethyl-thiomorpholine-3-carboxylic acid hydroxyamide;

4-[7-(2,4-Dichloro-benzoylamino)-dibenzofuran-2-sulfonyl]-2,2-dimethyl-thiomorpholine-3-carboxylic acid hydroxyamide;

4-[7-(2,5-Dimethoxy-benzoylamino)-dibenzofuran-2-sulfonyl]-2,2-dimethyl-thiomorpholine-3-carboxylic acid hydroxyamide;

2,2-Dimethyl-4-[7-(4-methyl-pentanoylamino)-dibenzofuran-2-sulfonyl]-thiomorpholine-3-carboxylic acid hydroxyamide;

4-[7-(Cyclopropanecarbonyl-amino)-dibenzofuran-2-sulfonyl]-2,2-dimethyl-thiomorpholine-3-carboxylic acid hydroxyamide;

Acetic acid [8-(3-hydroxycarbamoyl-2,2-dimethyl-thiomorpholine-4-sulfonyl)-dibenzofuran-3-ylcarbamoyl]-phenyl-methyl ester;

2,2-Dimethyl-4-{7-[(tricyclo[3.3.1]decanane-1-carbonyl)-amino]-dibenzofuran-2-sulfonyl}-thiomorpholine-3-carboxylic acid hydroxyamide;

2,2-Dimethyl-4-(7-pentanoylamino-dibenzofuran-2-sulfonyl)-thiomorpholine-3-carboxylic acid hydroxyamide;

4-[7-(2,2-Dimethyl-propionylamino)-dibenzofuran-2-sulfonyl]-2,2-dimethyl-thiomorpholine-3-carboxylic acid hydroxyamide;

2,2-Dimethyl-4-[7-((Z)-octadec-9-enoylamino)-dibenzofuran-2-sulfonyl]-thiomorpholine-3-carboxylic acid hydroxyamide;

N-[8-(3-Hydroxycarbamoyl-2,2-dimethyl-thiomorpholine-4-sulfonyl)-dibenzofuran-3-yl]-succinamic acid ethyl ester;

4-(7-Isobutyrylamino-dibenzofuran-2-sulfonyl)-2,2-dimethyl-thiomorpholine-3-carboxylic acid hydroxyamide;

4-(7-Isobutyrylamino-dibenzofuran-2-sulfonyl)-2,2-dimethyl-thiomorpholine-3-carboxylic acid hydroxyamide;

4-[7-(3-Chloro-benzoylamino)-dibenzofuran-2-sulfonyl]-2,2-dimethyl-thiomorpholine-3-carboxylic acid hydroxyamide;

2,2-Dimethyl-4-(7-nonanoylamino-dibenzofuran-2-sulfonyl)-thiomorpholine-3-carboxylic acid hydroxyamide;

2,2-Dimethyl-4-[7-(2-trifluoromethyl-benzoylamino)-dibenzofuran-2-sulfonyl]-thiomorpholine-3-carboxylic acid hydroxyamide;

2,2-Dimethyl-4-[7-(2-trifluoromethyl-benzoylamino)-dibenzofuran-2-sulfonyl]-thiomorpholine-3-carboxylic acid hydroxyamide;

2,2-Dimethyl-4-(7-octanoylamino-dibenzofuran-2-sulfonyl)-thiomorpholine-3-carboxylic acid hydroxyamide;

4-(7-Hexadecanoylamino-dibenzofuran-2-sulfonyl)-2,2-dimethyl-thiomorpholine-3-carboxylic acid hydroxyamide;

4-(7-Hexadecanoylamino-dibenzofuran-2-sulfonyl)-2,2-dimethyl-thiomorpholine-3-carboxylic acid hydroxyamide;

2,2-Dimethyl-4-[7-(2,2,3,3,4,4,5,5,6,6,7,7,8,8,8-pentadecafluoro-octanoylamino)-dibenzofuran-2-sulfonyl]-thiomorpholine-3-carboxylic acid hydroxyamide;

2,2-Dimethyl-4-[7-(2-phenoxy-acetylamino)-dibenzofuran-2-sulfonyl]-thiomorpholine-3-carboxylic acid hydroxyamide;

2,2-Dimethyl-4-[7-(2-phenoxy-acetylamino)-dibenzofuran-2-sulfonyl]-thiomorpholine-3-carboxylic acid hydroxyamide;

2,2-Dimethyl-4-(7-phenylacetylamino-dibenzofuran-2-sulfonyl)-thiomorpholine-3-carboxylic acid hydroxyamide;

2,2-Dimethyl-4-(7-propionylamino-dibenzofuran-2-sulfonyl)-thiomorpholine-3-carboxylic acid hydroxyamide;

2,2-Dimethyl-4-(7-tridecanoylamino-dibenzofuran-2-sulfonyl)-thiomorpholine-3-carboxylic acid hydroxyamide;

4-[7-(3,5-Dinitro-benzoylamino)-dibenzofuran-2-sulfonyl]-2,2-dimethyl-thiomorpholine-3-carboxylic acid hydroxyamide;

N-[8-(3-Hydroxycarbamoyl-2,2-dimethyl-thiomorpholine-4-sulfonyl)-dibenzofuran-3-yl]-malonamic acid ethyl ester;

N-[8-(3-Hydroxycarbamoyl-2,2-dimethyl-thiomorpholine-4-sulfonyl)-dibenzofuran-3-yl]-malonamic acid ethyl ester;

2,2-Dimethyl-4-[7-(2,2,2-trichloro-acetylamino)-dibenzofuran-2-sulfonyl]-thiomorpholine-3-carboxylic acid hydroxyamide;

2,2-Dimethyl-4-{7-[(thiophene-2-carbonyl)-amino]-dibenzofuran-2-sulfonyl}-thiomorpholine-3-carboxylic acid hydroxyamide;

2,2-Dimethyl-4-[7-(3-phenyl-propionylamino)-dibenzofuran-2-sulfonyl]-thiomorpholine-3-carboxylic acid hydroxyamide; or 4-[7-(2-Bromo-benzoylamino)-dibenzofuran-2-sulfonyl]-2,2-dimethyl-thiomorpholine-3-carboxylic acid hydroxyamide.

12. A pharmaceutical composition, comprising a compound of claim 1, or a pharmaceutically acceptable salt thereof, admixed with a pharmaceutically acceptable carrier, diluent, or excipient.

13. A pharmaceutical composition, comprising a compound of any one of claims 2, 6, 7, 8, 9, or 10, or a pharmaceutically acceptable salt thereof, admixed with a pharmaceutically acceptable carrier, diluent, or excipient.

14. A pharmaceutical composition, comprising a compound of claim 11, or a pharmaceutically acceptable salt thereof, admixed with a pharmaceutically acceptable carrier, diluent, or excipient.

15. A method for treating rheumatoid arthritis comprising administering to a patient in need of treatment an effective amount of a compound of claim 1, or a pharmaceutically acceptable salt thereof.

16. A method for treating osteoarthritis comp rising administering to a patient in need of treatment an effective amount of a compound of claim 1, or a pharmaceutically acceptable salt thereof.

* * * * *

UNITED STATES PATENT AND TRADEMARK OFFICE
CERTIFICATE OF CORRECTION

PATENT NO.   : 6,559,142 B2
DATED        : May 6, 2003
INVENTOR(S)  : O'Brien et al.

Page 1 of 1

It is certified that error appears in the above-identified patent and that said Letters Patent is hereby corrected as shown below:

<u>Column 33,</u>
Lines 55-57, delete the duplicate name
"4-(7-Decanoylamino-dibenzofuran-2-sulfonyl)-2,2-dimethyl-thiomorpholine-3-carboxylic acid hydroxyamide;".

<u>Column 34,</u>
Lines 46-48, delete the duplicate name
"4-(7-Isobutyrylamino-dibenzofuran-2-sulfonyl)-2,2-dimethyl-thiomorpholine-3-carboxylic acid hydroxyamide;".
Lines 58-60, delete the duplicate name
"2,2-Dimethyl-4-[7-(2-trifluoromethyl-benzoylamino)-dibenzofuran-2-sulfonyl]-thiomorpholine-3-carboxylic acid hydroxyamide;".

<u>Column 35,</u>
Lines 1-3, delete the duplicate name "4-(7-Hexadecanoylamino-dibenzofuran-2-sulfonyl)-2,2-dimethyl-thiomorpholine-3-carboxylic acid hydroxyamide;".
Lines 11-13, delete the duplicate name "2,2-Dimethyl-4-[7-(2-phenoxy-acetylamino)-dibenzofuran-2-sulfonyl]-thiomorpholine-3-carboxylic acid hydroxyamide;".
Lines 31-33, delete the duplicate name
"N-[8-(3-Hydroxycarbamoyl-2,2-dimethyl-thiomorpholine-4-sulfonyl)-dibenzofuran-3-yl]-malonamic acid ethyl ester;".

Signed and Sealed this

Twentieth Day of January, 2004

JON W. DUDAS
*Acting Director of the United States Patent and Trademark Office*